(12) United States Patent
Paul et al.

(10) Patent No.: US 8,728,077 B2
(45) Date of Patent: May 20, 2014

(54) HANDLE SET FOR ABLATION CATHETER WITH INDICATORS OF CATHETER AND TISSUE PARAMETERS

(75) Inventors: Saurav Paul, Minnetonka, MN (US); Kedar Ravindra Belhe, Minnetonka, MN (US); Hong Cao, Savage, MN (US); Chou Thao, Brooklyn Park, MN (US); James A. Hassett, Eden Prairie, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 596 days.

(21) Appl. No.: 12/096,069

(22) PCT Filed: Dec. 6, 2006

(86) PCT No.: PCT/US2006/061710
§ 371 (c)(1),
(2), (4) Date: Jun. 4, 2008

(87) PCT Pub. No.: WO2007/067937
PCT Pub. Date: Jun. 14, 2007

(65) Prior Publication Data
US 2008/0275465 A1  Nov. 6, 2008

Related U.S. Application Data

(60) Provisional application No. 60/748,234, filed on Dec. 6, 2006.

(51) Int. Cl.
*A61B 18/18* (2006.01)
*A61B 5/05* (2006.01)

(52) U.S. Cl.
USPC .............................. 606/49; 606/37; 600/547

(58) Field of Classification Search
USPC ................... 600/547; 606/27–32, 41, 49, 129
See application file for complete search history.

(56) References Cited

U.S. PATENT DOCUMENTS

| 5,230,349 A | 7/1993 | Langberg |
| 5,257,635 A | 11/1993 | Langberg |

(Continued)

FOREIGN PATENT DOCUMENTS

| EP | 1472976 | 11/2004 |
| EP | 1586281 | 4/2009 |

(Continued)

OTHER PUBLICATIONS

Avitall, Boaz et al.; "The Effects of Electrode-Tissue Contact on Radiofrequency Lesion Generation", *PACE*, vol. 20 Dec. 1997, 2899-2910.

(Continued)

*Primary Examiner* — Max Hindenburg
*Assistant Examiner* — Adam Eiseman
(74) *Attorney, Agent, or Firm* — Marsh Fischmann & Breyfogle LLP

(57) ABSTRACT

An electrode coupling output system provides indication to the physician, via electrode guidance instrumentation, concerning the electrical coupling of an electrode, such as an ablative or mapping electrode, with a patient. The output can be provided to the physician via an output device incorporated into the handle set of the electrode catheter. For example, a visual, audio or mechanical output can be provided via the handle set. Additionally or alternatively, the output can be provided to the physician via a navigation system. The indication may be provided by changing the color or other display characteristics of the electrode on the navigation system display or by way of providing a waveform indicating the electrode coupling. In this manner, electrode coupling information is provided to a physician in a manner that minimizes physician distraction.

14 Claims, 29 Drawing Sheets

(56) References Cited

U.S. PATENT DOCUMENTS

| | | | |
|---|---|---|---|
| 5,341,807 A * | 8/1994 | Nardella | 600/381 |
| 5,447,529 A | 9/1995 | Marchlinski et al. | |
| 5,582,609 A * | 12/1996 | Swanson et al. | 606/39 |
| 5,588,432 A | 12/1996 | Crowley et al. | |
| 5,673,704 A | 10/1997 | Marchlinski et al. | |
| 5,702,386 A * | 12/1997 | Stern et al. | 606/34 |
| 5,730,127 A * | 3/1998 | Avitall | 600/374 |
| 5,759,159 A | 6/1998 | Masreliez | |
| 5,836,990 A | 11/1998 | Li | |
| 6,001,093 A * | 12/1999 | Swanson et al. | 606/41 |
| 6,129,669 A | 10/2000 | Panescu et al. | |
| 6,171,304 B1 | 1/2001 | Netherly et al. | |
| 6,217,574 B1 | 4/2001 | Webster et al. | |
| 6,337,994 B1 | 1/2002 | Stoianovici et al. | |
| 6,391,024 B1 | 5/2002 | Sun et al. | |
| 6,423,057 B1 | 7/2002 | He et al. | |
| 6,490,474 B1 | 12/2002 | Willis et al. | |
| 6,569,160 B1 | 5/2003 | Goldin et al. | |
| 6,755,790 B2 * | 6/2004 | Stewart et al. | 600/466 |
| 6,780,182 B2 * | 8/2004 | Bowman et al. | 606/41 |
| 7,819,870 B2 * | 10/2010 | Thao et al. | 606/41 |
| 2001/0034501 A1 | 10/2001 | Tom | |
| 2002/0022836 A1 | 2/2002 | Goble et al. | |
| 2002/0068931 A1 | 6/2002 | Wong et al. | |
| 2002/0077627 A1 * | 6/2002 | Johnson et al. | 606/41 |
| 2003/0065364 A1 | 4/2003 | Wellman et al. | |
| 2003/0093069 A1 | 5/2003 | Panescu et al. | |
| 2003/0100823 A1 | 5/2003 | Kipke et al. | |
| 2004/0078058 A1 | 4/2004 | Holmstrom et al. | |
| 2004/0087975 A1 * | 5/2004 | Lucatero et al. | 606/139 |
| 2004/0243018 A1 | 12/2004 | Organ et al. | |
| 2005/0054944 A1 | 3/2005 | Nakada et al. | |
| 2005/0222554 A1 | 10/2005 | Wallace et al. | |
| 2007/0100332 A1 * | 5/2007 | Paul et al. | 606/41 |

FOREIGN PATENT DOCUMENTS

| | | |
|---|---|---|
| WO | WO-98/46149 | 10/1998 |
| WO | WO-00/78239 | 12/2000 |

OTHER PUBLICATIONS

Panescu, Dorin et al., "Expandable-collapsible electrode structures made of electrically conductive material", US2003-0093069 A1 May 15, 2003.

Tom, Curtis P., "Pressure sensor for therapeutic delivery device and method", US2001-0034501 A1 Oct. 25, 2001.

Wellman, Parris S. et al., "Expandable intracardiac return electrode and method of use", US2003-0065364 A1 Apr. 3, 2003.

\* cited by examiner

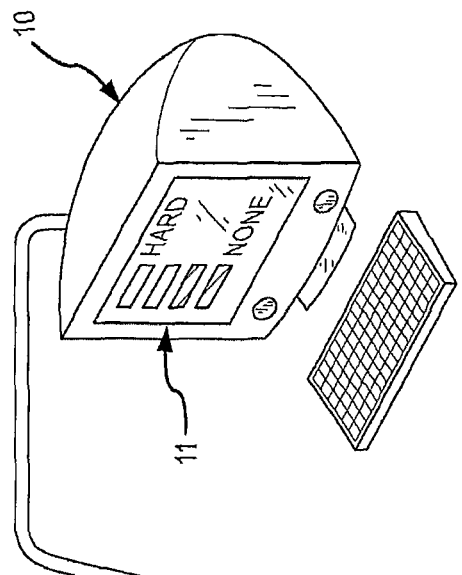
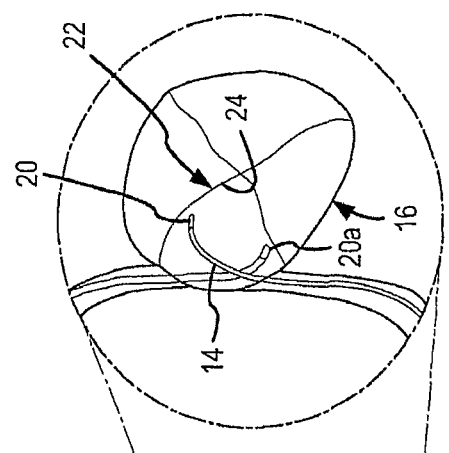
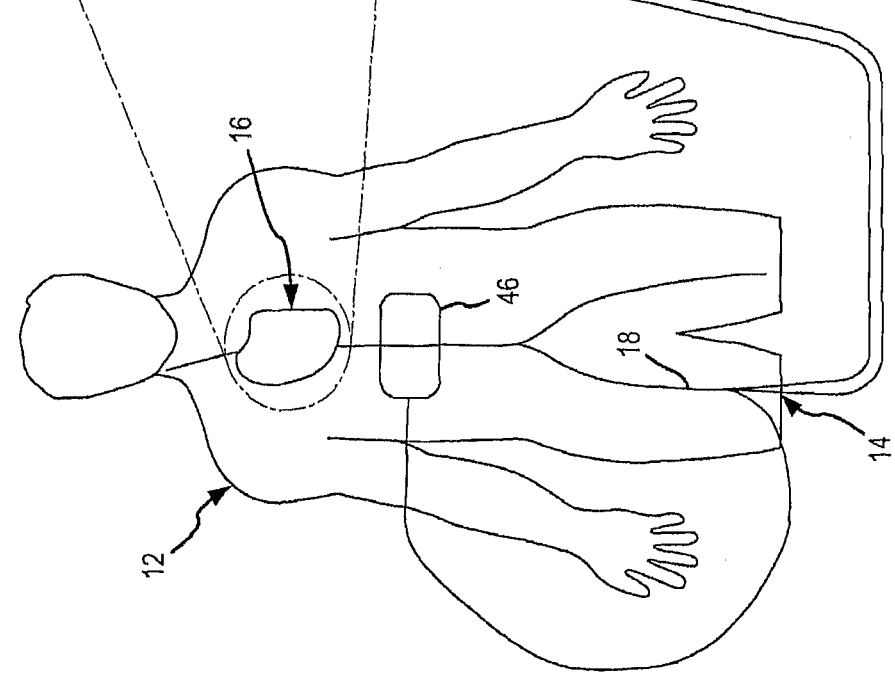
FIG.1a
FIG.1

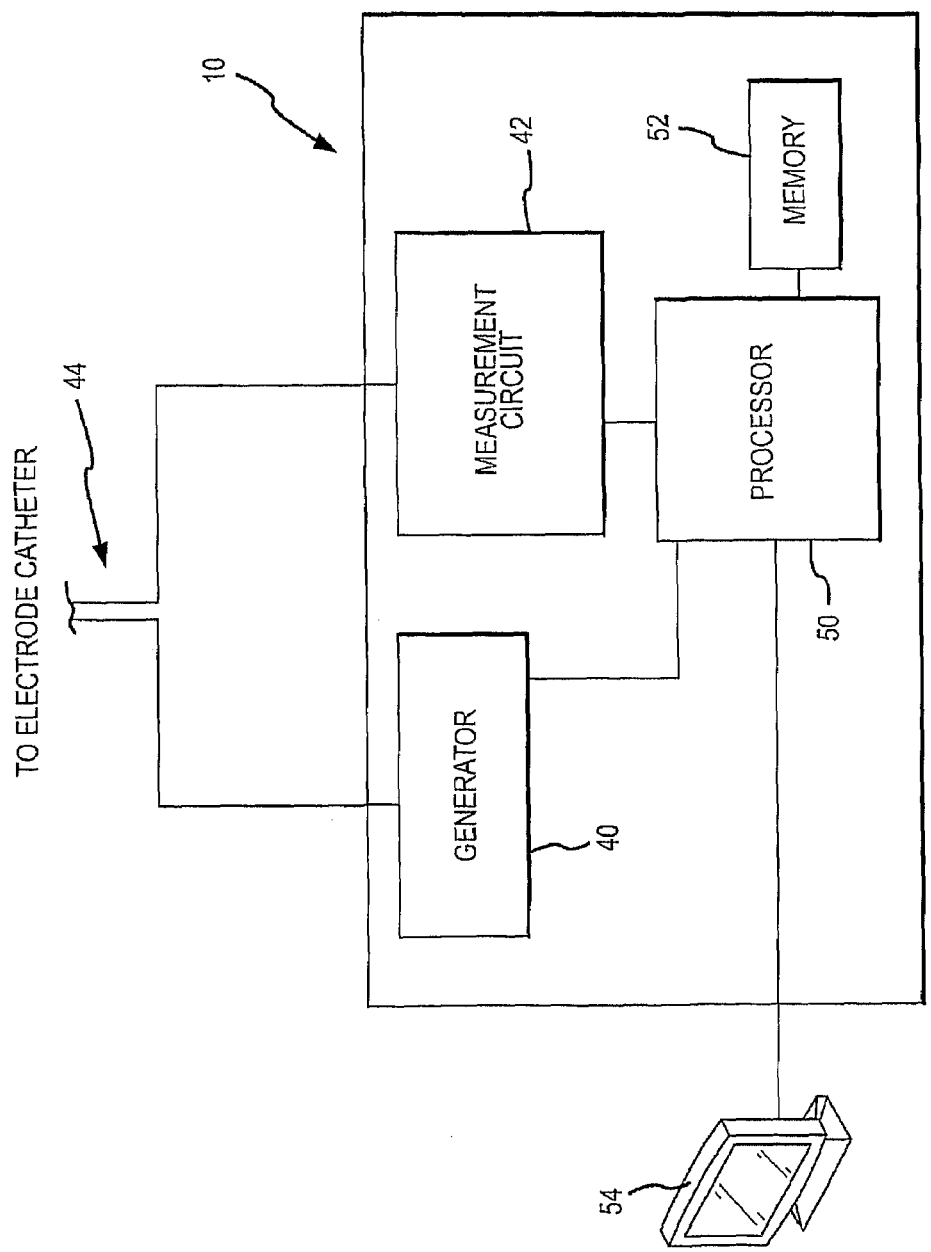

HANDLE SET FOR ABLATION CATHETER WITH INDICATORS OF CATHETER AND TISSUE PARAMETERS

CROSS-REFERENCE TO RELATED APPLICATION

This application is a national stage of international application no. PCT/US2006/061710, filed 6 Dec. 2006, which claims the benefit of U.S. provisional application No. 60/748,234, filed on 6 Dec., 2005, both of which are incorporated herein by reference. This application is also related to international application nos. PCT/US2006/046565, PCT/US2006/061716, PCT/US2006/061712, PCT/US2006/061714, PCT/US2006/061711, PCT/US2006/061713 and PCT/US2006/046816, all filed 6 Dec. 2006 ("international applications"). The international applications are incorporated herein by reference.

BACKGROUND OF THE INVENTION a. Field of the Invention

The instant invention is directed toward an electrode catheter and a method for using the electrode catheter for tissue ablation. In particular, the electrode catheter of the present invention may comprise a circuit to assess electrode-tissue contact and electrical coupling for applying ablative energy (e.g., RF energy) to target tissue.

b. Background Art

It is well known that benefits may be gained by forming lesions in tissue if the depth and location of the lesions being formed can be controlled. In particular, it can be desirable to elevate tissue temperature to around 50° C. until lesions are formed via coagulation necrosis, which changes the electrical properties of the tissue. For example, lesions may be formed at specific locations in cardiac tissue via coagulation necrosis to lessen or eliminate undesirable atrial fibrillations.

Several difficulties may be encountered, however, when attempting to form lesions at specific locations using some existing ablation electrodes. One such difficulty encountered with existing ablation electrodes is how to ensure adequate tissue contact and electrical coupling. Electrode-tissue contact is not readily determined using conventional techniques such as fluoroscopy. Instead, the physician determines electrode-tissue contact based on his/her experience using the electrode catheter. Such experience only comes with time, and may be quickly lost if the physician does not use the electrode catheter on a regular basis. In addition, when forming lesions in a heart, the beating of the heart further complicates matters, making it difficult to determine and maintain sufficient contact pressure between the electrode and the tissue for a sufficient length of time to form a desired lesion. If the contact between the electrode and the tissue cannot be properly maintained, a quality lesion is unlikely to be formed. Similarly, information on electrical coupling between the electrode and the target tissue is not readily available a priori to determine how much ablative energy may be absorbed in the tissue during ablation. Instead, the physician uses generalized pre-determined ablation parameters, such as power and duration, based on his/her experience to perform ablation procedures with the electrode catheter. Such experience may lead to deficiencies, inefficiencies and complications, such as inadequate lesion formation, premature high impedance shut-off, tissue charring, and thrombus formation.

BRIEF SUMMARY OF THE INVENTION

The present invention relates to providing an indication to the physician, via electrode guidance instrumentation, concerning the electrical coupling of an electrode, such as an ablative electrode or mapping electrode, with the patient. During an electrode catheter procedure, a physician uses electrode guidance instrumentation to control the positioning of an electrode. This guidance instrumentation generally includes a navigation system for monitoring electrode position and a manipulation system for positioning the electrode. The manipulation system may be manually or robotically operated. The navigation system may provide real-time visualization of electrode movements and position in relation to physiological structure of the patient. In manual implementations, the manipulation system may include a handle set for advancing, withdrawing, rotating and otherwise positioning the electrode.

It has been recognized that it is desirable to provide an indication concerning electrode coupling with minimal distraction to the physician. This is particularly the case where the system is used not only for initially establishing a desired electrode position for a procedure, but also for monitoring electrode position during the procedure. This can be accomplished, in accordance with the present invention, by providing an indication via the guidance instrumentation, e.g., via the handle set of the manipulation system or via a monitor of the navigation system. In this manner, the physician can receive continuously or periodically (occasionally) updated electrode coupling information during a medical procedure while the physician's attention remains substantially fully directed to the medical procedure.

In accordance with one aspect of the present invention, a method and apparatus ("utility") is provided that supplies an indication to the physician, via electrode guidance instrumentation, concerning the electrical coupling of an electrode. The utility involves establishing an electrical coupling monitoring system for evaluating an electrode coupling relationship. Any suitable monitoring system may be used in this regard, including systems based on impedance, phase angle, mechanical vibration or mechanical deformation measurements. The monitoring system is operative to distinguish between at least two different electrode coupling levels (e.g., insufficient or sufficient coupling for the procedure at issue) and may distinguish between more than two electrode coupling levels (e.g., insufficient coupling, sufficient coupling and elevated coupling). In one implementation, the electrical coupling monitoring system employs a phase angle technology where different electrode coupling levels are associated with different phase angle ranges. The utility further involves operating an electrode coupling assessment system in connection with a medical procedure to identify a level of electrode coupling. For example, the assessment system may be operated prior to initiation of an ablative or mapping procedure to analyze electrode coupling. Additionally or alternatively, the assessment system may be operated continuously or periodically during a medical procedure to monitor electrode coupling. An output is then provided indicating the identified level of electrode coupling. In particular, the output is provided via instrumentation used by the physician in guiding the electrode. For example, an audio, visual or mechanical output may be provided via the handle set of the electrode catheter. Additionally or alternatively, an output may be provided in connection with a navigation system used in connection with the medical procedure.

In accordance with another aspect of the present invention, an output device is incorporated into the handle set of an electrode catheter to provide information of interest to a physician. As noted above, it is desirable to provide information to a physician during an electrode catheter procedure that minimizes distraction to the physician. This can be accomplished in accordance with the present aspect of the invention by incorporating an output device into the handle set of the catheter. The information of interest may relate to a patient parameter, an instrument parameter or other value. An associated utility involves operating a processor to monitor a parameter associated with the electrode catheter procedure; analyzing the parameter to identify a condition of interest; and, in response to identifying the condition of interest, providing an indication via the output device incorporated into the handle set. For example, the output device may include a visual output device such as an LED display, an audio output device such as a tone generator, and a mechanical output device such as a vibration generator. The output device can output a simple yes/no indication in relation to the condition of interest (e.g., by activating or deactivating the visual, audio and/or mechanical output device) or can provide an indication regarding a range of levels related to the condition of interest. In the latter regard, a visual output device may include an LED bar graph, an audio output device may be controlled to vary a volume or pitch of a tone, or a vibration generator may change a frequency or amplitude of vibration. In this manner, an indication is provided to the physician regarding the condition of interest with minimal distraction from the electrode catheter procedure.

In accordance with a still further aspect of the present invention, an electrode catheter system is provided that allows for providing electrode coupling information with minimal distraction. An associated utility involves: an electrode adapted to apply electrical energy; a catheter for enabling the electrode to be remotely operated by a physician; guidance instrumentation for guiding the electrode relative to the physiological structure of a patient; and a processor for receiving signal information and determining a level of electrical coupling between the electrode and the patient. The guidance instrumentation includes at least a navigation system for use in monitoring a position of the electrode and a manipulation for use in controlling a position of the electrode. The processor is further operative to control the guidance instrumentation to provide an indication of the level of electrode coupling. In this regard, the processor can distinguish between a least two different levels of electrode coupling. In one implementation, the processor can distinguish between multiple levels of electrode coupling, including a level indicating elevated coupling that may be associated with the potential for penetrating or perforating tissue of interest. Such penetration may be desired or undesired. In either event, an indication of such elevated coupling can be useful to a physician or control system. The various levels of electrode coupling may be determined by any suitable technology. In one implementation, the levels are distinguished based on a phase angle analysis.

The foregoing and other aspects, features, details, utilities, and advantages of the present invention will be apparent from reading the following description and claims, and from reviewing the accompanying drawings.

BRIEF DESCRIPTION OF THE DRAWINGS

FIG. 1 is a diagrammatic illustration of an exemplary tissue ablation system which may be implemented to assess electrode-tissue contact during a tissue ablation procedure for a patient.

FIG. 1a is a detailed illustration of the patient's heart in FIG. 1, showing the electrode catheter after it has been moved into the patient's heart.

FIG. 3 is a high-level functional block diagram showing the exemplary tissue ablation system of FIG. 1 in more detail.

DETAILED DESCRIPTION OF THE INVENTION

Figure 2A:
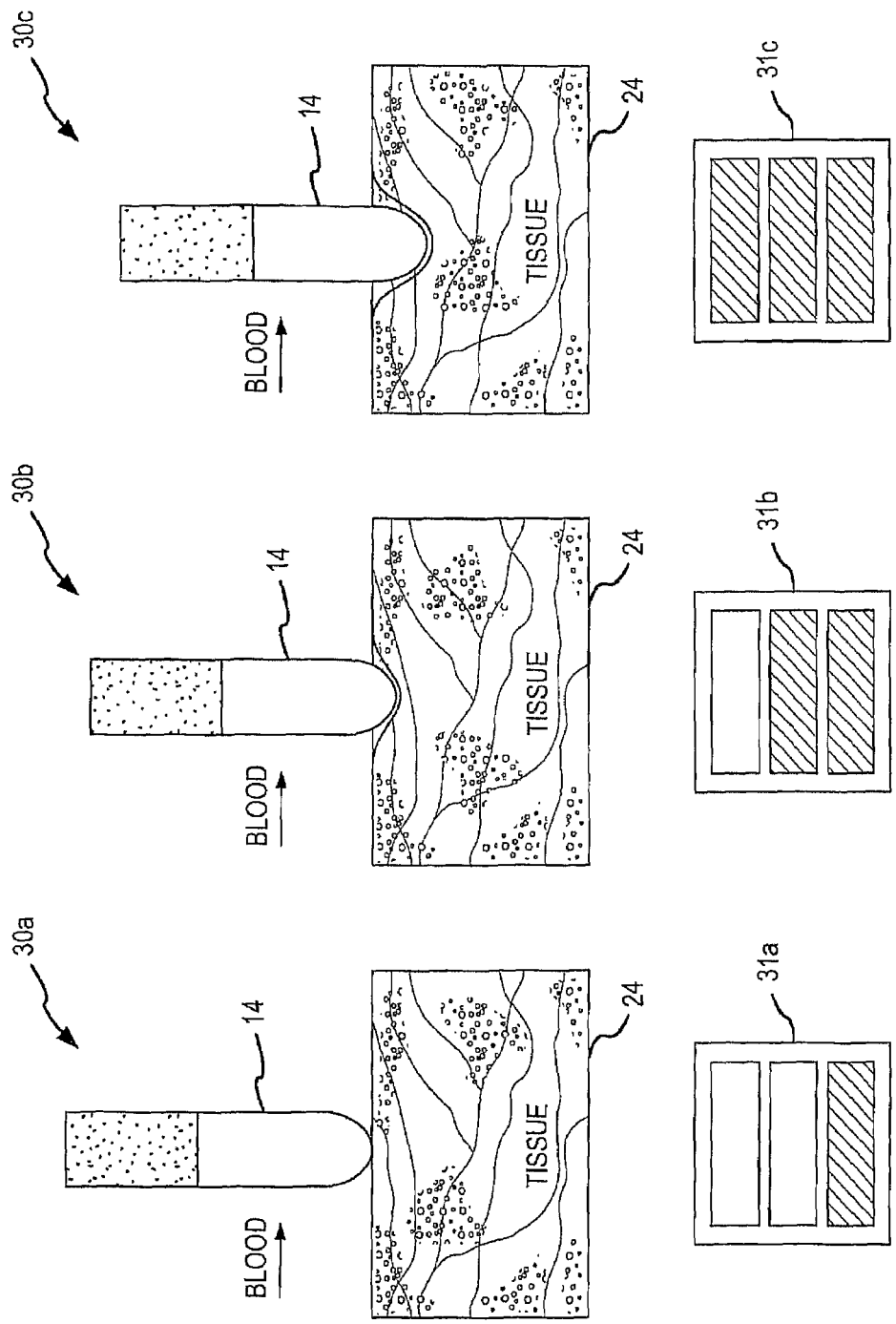
FIG. 2a illustrates exemplary levels of electrical contact or coupling between the electrode catheter and a target tissue.

The present invention relates to providing an indication regarding a condition of interest, e.g., a level of electrode coupling, to a physician via guidance instrumentation of an electrode catheter system. While such an indication may be provided in connection with various parameters of interest in connection with an electrode catheter procedure and, specifically, in connection with a variety of electrode coupling assessment technologies, certain advantage are achieved by using an assessment technology capable of accurately identifying multiple electrode coupling levels such as a phase angle technology. In the following description, certain phase angle-related technologies are first described. Thereafter, various mechanisms for outputting information to the physician are described in detail.

FIG. 1 is a diagrammatic illustration of an exemplary electrode catheter system 10 which may be implemented to assess electrode-tissue contact during a tissue ablation procedure for a patient 12. Catheter system 10 may include an electrode catheter 14, which may be inserted into the patient 12, e.g., for forming ablative lesions inside the patient's heart 16. During an exemplary ablation procedure, a user (e.g., the patient's physician or a technician) may insert the electrode catheter 14 into one of the patient's blood vessels 18, e.g., through the leg (as shown in FIG. 1) or the patient's neck. The user, guided by a real-time fluoroscopy imaging device (not shown), moves the electrode catheter 14 into the patient's heart 16 (as shown in more detail in FIG. 1a).

When the electrode catheter 14 reaches the patient's heart 16, electrodes 20 at the tip of the electrode catheter 14 may be implemented to electrically map the myocardium 22 (i.e., muscular tissue in the heart wall) and locate a target tissue 24. After locating the target tissue 24, the user must move the electrode catheter 14 into contact and electrically couple the catheter electrode 14 with the target tissue 24 before applying ablative energy to form an ablative lesion or lesions. The electrode-tissue contact refers to the condition when the catheter electrode 14 physically touches the target tissue 24 thereby causing a mechanical coupling between the catheter electrode 14 and the target tissue 24. Electrical coupling refers to the condition when a sufficient portion of electrical energy passes from the catheter electrode 14 to the target tissue 24 so as to allow efficient lesion creation during ablation. For target tissues with similar electrical and mechanical properties, electrical coupling includes mechanical contact. That is, mechanical contact is a subset of electrical coupling. Thus, the catheter electrode may be substantially electrically coupled with the target tissue without being in mechanical contact, but not vice-versa. In other words, if the catheter electrode is in mechanical contact, it is also electrically coupled. The range or sensitivity of electrical coupling, however, changes for tissues with different electrical properties. For example, the range of electrical coupling for electrically conductive myocardial tissue is different from the vessel walls. Likewise, the range or sensitivity of electrical coupling also changes for tissues with different mechanical properties, such as tissue compliance. For example, the range of electrical coupling for the relatively more compliant smooth atrial wall is different from the relatively less compliant pectinated myocardial tissue. The level of contact and electrical coupling are often critical to form sufficiently deep ablative lesions on the target tissue 24 without damaging surrounding tissue in the heart 16. The catheter system 10 may be implemented to measure impedance at the electrode-tissue interface and assess the level of contact (illustrated by display 11) between the electrode catheter 14 and the target tissue 24, as described in more detail below.

Figure 2B:
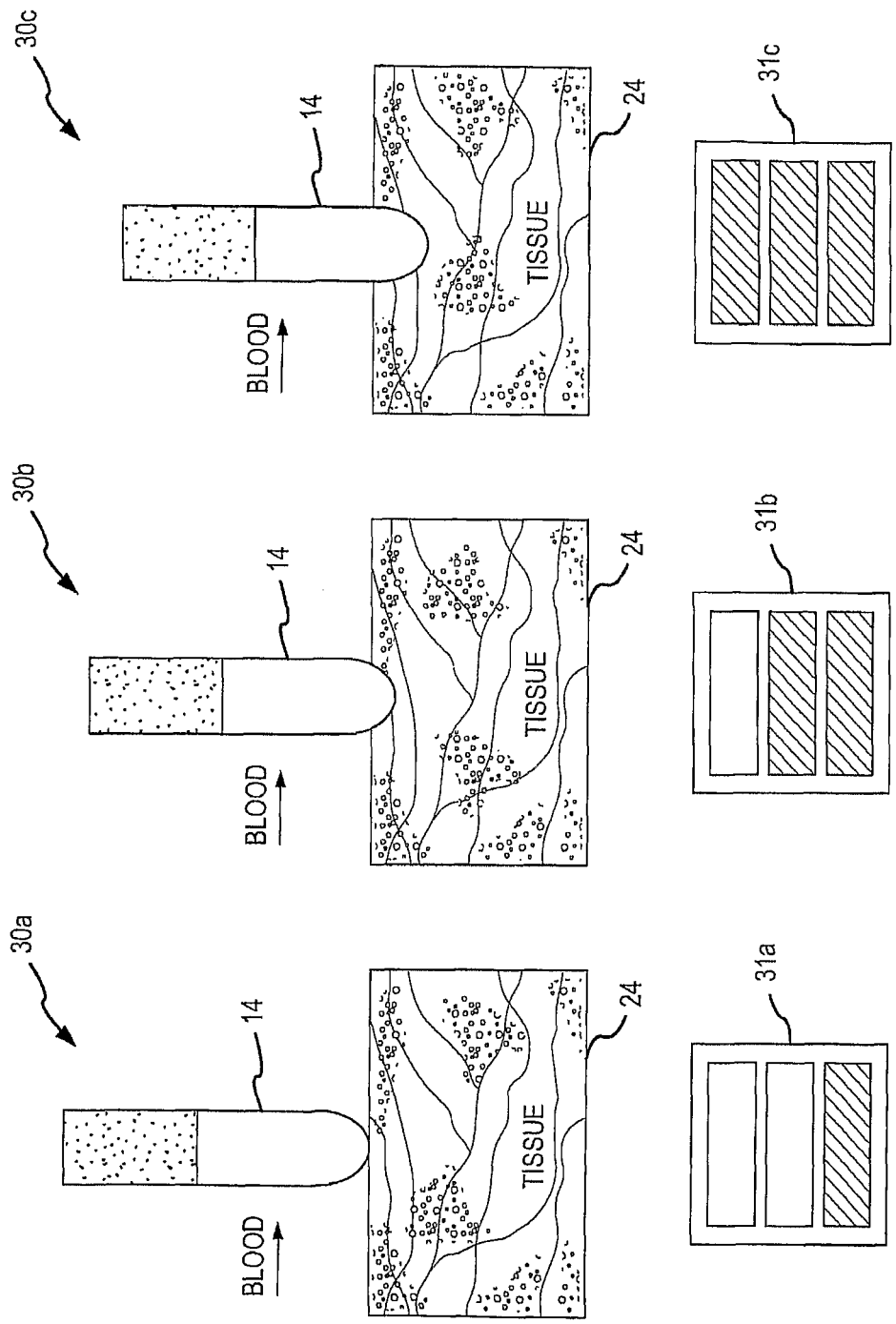
FIG. 2b illustrates exemplary levels of mechanical contact or coupling between the electrode catheter and a target tissue.

FIG. 2a illustrates exemplary levels of electrical contact or coupling between an electrode catheter 14 and a target tissue 24. FIG. 2b illustrates exemplary levels of mechanical contact or coupling between an electrode catheter 14 and a target tissue 24. Exemplary levels of contact or coupling may include "little or no contact" as illustrated by contact condition 30a, "light to medium contact" as illustrated by contact condition 30b, and "hard contact" as illustrated by contact condition 30c. In an exemplary embodiment, the catheter system 10 may be implemented to display or otherwise output the contact condition for the user, e.g., as illustrated by light arrays 31a-c corresponding to contact conditions 30a-c, respectively.

Contact condition 30a ("little or no contact") may be experienced before the electrode catheter 14 comes into contact with the target tissue 24. Insufficient contact may inhibit or even prevent adequate lesions from being formed when the electrode catheter 14 is operated to apply ablative energy. However, contact condition 30c ("hard contact") may result in the formation of lesions which are too deep (e.g., causing perforations in the myocardium 22) and/or the destruction of tissue surrounding the target tissue 24. Accordingly, the user may desire contact condition 30b ("light to medium contact").

It is noted that the exemplary contact or coupling conditions 30a-c in FIG. 2a-b are shown for purposes of illustration and are not intended to be limiting. Other contact or coupling conditions (e.g., finer granularity between contact conditions) may also exist and/or be desired by the user. The definition of such contact conditions may depend at least to some extent on operating conditions, such as, the type of target tissue, desired depth of the ablation lesion, and operating frequency of the RF radiation, to name only a few examples.

FIG. 3 is a high-level functional block diagram showing the catheter system 10 in more detail as it may be implemented to assess contact or coupling conditions for the electrode catheter 14. It is noted that some of the components typical of conventional tissue ablation systems are shown in simplified form and/or not shown at all in FIG. 1 for purposes of brevity. Such components may nevertheless also be provided as part of, or for use with the catheter system 10. For example, electrode catheter 14 may include a handle portion, a fluoroscopy imaging device, and/or various other controls, to name only a few examples. Such components are well understood in the medical devices arts and therefore further discussion herein is not necessary for a complete understanding of the invention.

Exemplary catheter system 10 may include a generator 40, such as, e.g., a radio frequency (RF) generator, and a measurement circuit 42 electrically connected to the electrode catheter 14 (as illustrated by wires 44 to the electrode catheter). The electrode catheter 14 may also be electrically grounded, e.g., through grounding patch 46 affixed to the patient's arm or chest (as shown in FIG. 1).

Generator 40 may be operated to emit electrical energy (e.g., RF current) near the tip of the electrode catheter 14. It is noted that although the invention is described herein with reference to RF current, other types of electrical energy may also be used for assessing contact conditions.

In an exemplary embodiment, generator 40 emits a so-called "pinging" (e.g., low) frequency as the electrode catheter 14 approaches the target tissue 24. The "pinging" frequency may be emitted by the same electrode catheter that is used to apply ablative energy for lesion formation. Alternatively, a separate electrode catheter may be used for applying the "pinging" frequency. In such an embodiment, the separate electrode may be in close contact with (or affixed to) the electrode for applying ablative energy so that a contact or coupling condition can be determined for the electrode which will be applying the ablative energy.

The resulting impedance at the electrode-tissue interface may be measured during contact or coupling assessment (or "pinging") using a measurement circuit 42. In an exemplary embodiment, the measurement circuit 42 may be a conventionally available resistance-capacitance-inductance (RCL) meter. Another exemplary measurement circuit which may be implemented for determining the phase angle component is also described in more detail below with reference to FIG. 5. Still other measurement circuits 42 may be implemented and the invention is not limited to use with any particular type or configuration of measurement circuit.

The reactance and/or phase angle component of the impedance measurements may be used to determine a contact or coupling condition. The contact or coupling condition may then be conveyed to the user in real-time for achieving the desired level of contact or coupling for the ablation procedure. For example, the contact or coupling condition may be displayed for the user on a light array (e.g., as illustrated in FIG. 2a-b).

After the user has successfully guided the electrode catheter 14 into the desired contact or coupling condition with the target tissue 24, a generator, such as generator 40 or a second generator, may be operated to generate ablative (e.g., high frequency) energy for forming an ablative lesion or lesions on the target tissue 24. In an exemplary embodiment, the same generator 40 may be used to generate electrical energy at various frequencies both for the impedance measurements (e.g., "pinging" frequencies) and for forming the ablative lesion. In alternative embodiments, however, separate generators or generating units may also be implemented without departing from the scope of the invention.

In an exemplary embodiment, measurement circuit 42 may be operatively associated with a processor 50 and memory 52 to analyze the measured impedance. By way of example, processor 50 may determine a reactance and/or phase angle component of the impedance measurement, and based on the reactance component and/or phase angle, the processor 50 may determine a corresponding contact or coupling condition for the electrode catheter 14. In an exemplary embodiment, contact or coupling conditions corresponding to various reactance and/or phase angles may be predetermined, e.g., during testing for any of a wide range of tissue types and at various frequencies. The contact or coupling conditions may be stored in memory 52, e.g., as tables or other suitable data structures. The processor 50 may then access the tables in memory 42 and determine a contact or coupling condition corresponding to impedance measurement based on the reactance component and/or phase angle. The contact or coupling condition may be output for the user, e.g., at display device 54.

It is noted, that the catheter system 10 is not limited to use with processor 50 and memory 52. In other embodiments, analog circuitry may be implemented for assessing contact conditions based on the impedance measurement and for outputting a corresponding contact condition. Such circuitry may be readily provided by one having ordinary skill in the electronics arts after having become familiar with the teachings herein, and therefore further discussion is not needed.

It is also noted that display device 54 is not limited to any particular type of device. For example, display device 54 may be a computer monitor such as a liquid-crystal display (LCD). Alternatively, display device may be implemented as a light array, wherein one or more light emitting diodes (LED) are activated in the light array to indicate a contact condition (e.g., more lights indicating more contact). Indeed, any suitable output device may be implemented for indicating contact conditions to a user, and is not limited to a display device. For example, the contact condition may be output to the user as an audio signal or tactile feedback (e.g., vibrations) on the handle of the electrode catheter.

It is further noted that the components of catheter system 10 do not need to be provided in the same housing. By way of example, measurement circuit 42 and/or processor 50 and memory 52 may be provided in a handle portion of the electrode catheter 14. In another example, at least part of the measurement circuit 42 may be provided elsewhere in the electrode catheter 14 (e.g., in the tip portion). In still other examples, processor 50, memory 52, and display device 54 may be provided as a separate computing device, such as a personal desktop or laptop computer which may be operatively associated with other components of the catheter system 10.

Figure 4:
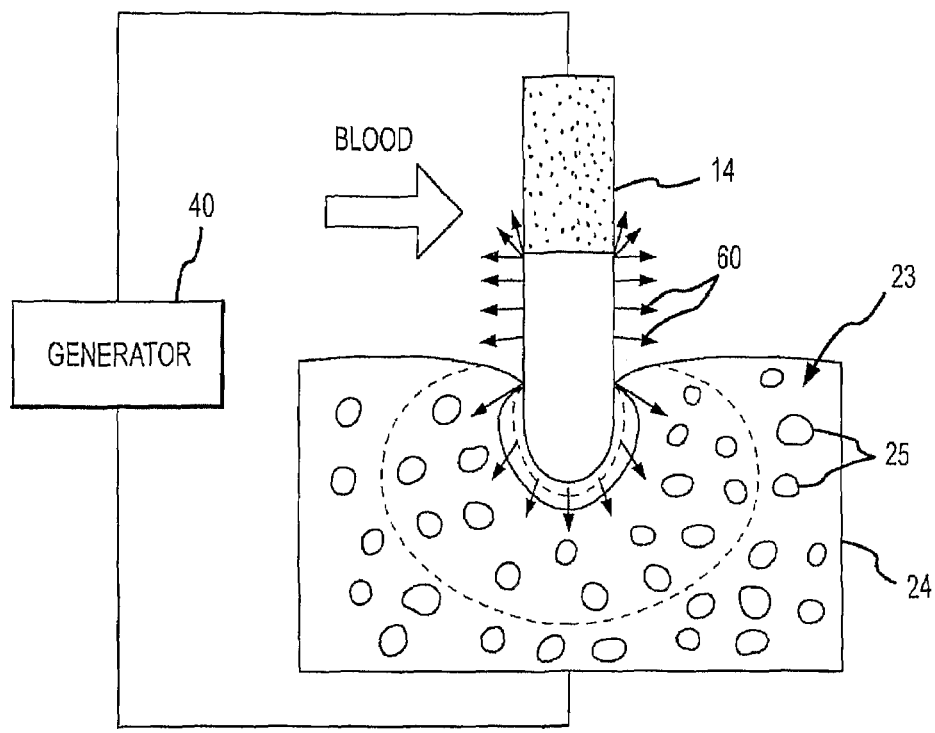
FIG. 4 is a model of the electrode catheter in contact with (or coupled to) target tissue.
Figure 4A:
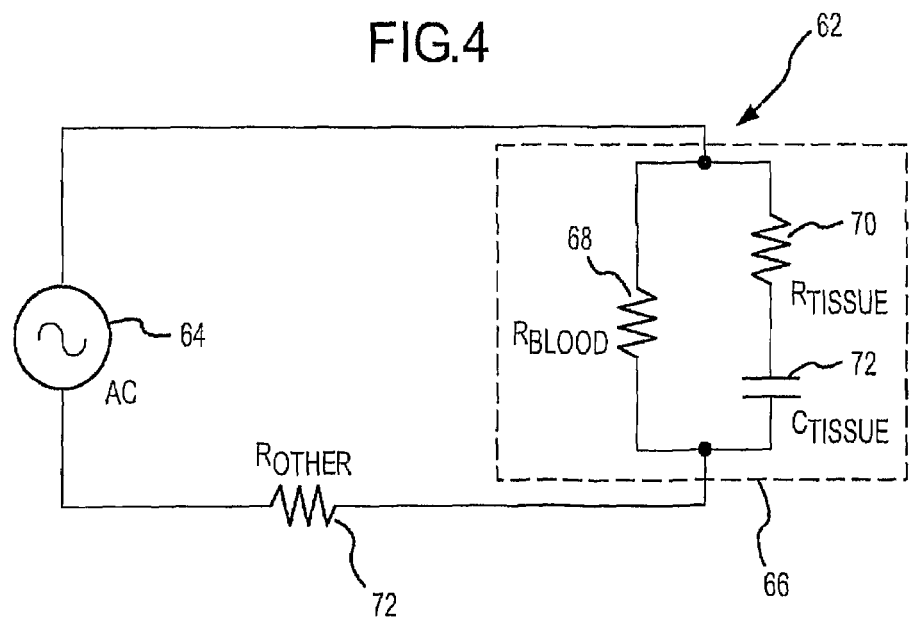
FIG. 4a is a simplified electrical circuit for the model shown in FIG. 4.

Assessing a contact or coupling condition between the electrode catheter 14 and target tissue 24 based on impedance measurements at the electrode-tissue interface may be better understood with reference to FIGS. 4 and 4a. FIG. 4 is a model of the electrode catheter 14 in contact with (or coupled to) target tissue 24. The electrode catheter 14 is electrically connected to the generator 40 (e.g., an RF generator). In an exemplary embodiment, the circuit may be completed through the target tissue 24, showing that current flows through the blood, myocardium, and other organs to the reference electrode, such as a grounding patch 46 on the patient's body (FIG. 1).

As described above, the generator 40 may be operated to generate electrical energy for emission by the electrode catheter 14. Emissions are illustrated in FIG. 4 by arrows 60. Also as described above, generator 40 may emit a "pinging" frequency as the electrode catheter 14 approaches the target tissue 24 for assessing electrode-tissue contact or coupling. In an exemplary embodiment, this "pinging" frequency may be selected such that inductive, capacitive, and resistive effects other than those at the blood-tissue interface do not appreciably affect the impedance measurements.

In an exemplary application, capacitive effects of the blood and at the electrode-blood interface (e.g., between the metal electrode catheter and the blood) were found be minimal or even non-existent at frequencies higher than about 50 kHz. Stray inductance (e.g., due to the relatively thin catheter wires), capacitance and resistance at the electrode interface, and capacitance effects of other organs (e.g., the lungs) were also found to be minimal or even non-existent at frequencies higher than about 50 kHz.

In addition, it was found that resistive effects dominate at the blood-tissue interface for frequencies below 50 kHz because the current flows into the target tissue 24 primarily via the interstitial fluid spaces 23, and the cell membranes 25

(e.g., bi-lipids or "fat") act as an insulator. However, at frequencies greater than about 50 kHz, the cell membranes 25 become conductive, and electrical current penetrates the target tissue 24 through both the interstitial fluid spaces 23 and the cell membranes 25. Accordingly, the cell membranes act as "capacitors" and the resistive effects are reduced at frequencies above about 50 kHz.

To avoid a risk of creating an ablation lesion during contact or coupling assessment, it can be desirable to use a low amount of current and power. A presently preferred range for a current of less than 1 mA is a working frequency in the 50~500 kHz range.

The frequency choice is mostly based on physiological aspect and engineering aspect and is within the purview of one of ordinary skill in the art. For physiological aspect, lower frequencies can introduce measurement errors due to electrode-electrolyte interface. When frequency goes higher to MHz range or above, the parasitic capacitance can become significant. It is noted, however, that the invention is not limited to use at any particular frequency or range of frequencies. The frequency may depend at least to some extent on operational considerations, such as, e.g., the application, the type of target tissue, and the type of electrical energy being used, to name only a few examples.

Assuming, that a desired frequency has been selected for the particular application, the model shown in FIG. 4 may be further expressed as a simplified electrical circuit 62, as shown in FIG. 4a. In the circuit 62, generator 40 is represented as an AC source 64. As discussed above, capacitance and resistance at the blood-tissue interface dominate impedance measurements at low frequency operation such as may be used for assessing electrode-tissue contact. Accordingly, other capacitive, inductive, and resistive effects may be ignored and the capacitive-resistive effects at the blood-tissue interface may be represented in circuit 62 by a resistor-capacitor (R-C) circuit 66.

The R-C circuit 66 may include a resistor 68 representing the resistive effects of blood on impedance, in parallel with a resistor 70 and capacitor 72 representing the resistive and capacitive effects of the target tissue 24 on impedance. When the electrode catheter 14 has no or little contact with the target tissue 24, resistive effects of the blood affect the R-C circuit 66, and hence also affect the impedance measurements. As the electrode catheter 14 is moved into contact with the target tissue 24, however, the resistive and capacitive effects of the target tissue 24 affect the R-C circuit 66, and hence also affect the impedance measurements.

The effects of resistance and capacitance on impedance measurements may be better understood with reference to a definition of impedance. Impedance (Z) may be expressed as:

$$Z = R + jX$$

where:
R is resistance from the blood and/or tissue;
j an imaginary number indicating the term has a phase angle of +90 degrees; and
X is reactance from both capacitance and inductance.

It is observed from the above equation that the magnitude of the reactance component responds to both resistive and capacitive effects of the circuit 62. This variation corresponds directly to the level of contact or coupling at the electrode-tissue interface, and therefore may be used to assess the electrode-tissue contact or coupling. By way of example, when the electrode catheter 14 is operated at a frequency of 100 kHz and is primarily in contact with the blood, the impedance is purely resistive and the reactance (X) is close to 0 Ohms. When the electrode catheter 14 contacts the target tissue, the reactance component becomes negative. As the level of contact or coupling is increased, the reactance component becomes more negative.

Alternatively, contact or coupling conditions may be determined based on the phase angle. Indeed, determining contact or coupling conditions based on the phase angle may be preferred in some applications because the phase angle is represented as a trigonometric ratio between reactance and resistance. Although the magnitude of the reactance component may be different under varying conditions (e.g., for different patients), the phase angle is a relative measurement which tends to be insensitive to external conditions.

In an exemplary embodiment, the phase angle may be determined from the impedance measurements (e.g., by the processor 50 in FIG. 3). That is, impedance may be expressed as:

$$Z = |Z| \angle \phi$$

where:
|Z| is the magnitude of the impedance; and
$\phi$ is the phase angle.
The terms |Z| and $\phi$ may further be expressed as:

$$|Z| = \sqrt{R^2 + X^2} \text{ ; and}$$

$$\tan\phi = \frac{X}{R}$$

The phase angle also corresponds directly to the level of contact or coupling at the electrode-tissue interface, and therefore may be used to assess the electrode-tissue contact or coupling. By way of example, when the electrode catheter 14 is operated at a frequency of 100 kHz and is primarily in contact with the blood, the phase angle is close to zero (0). When the electrode catheter 14 contacts the target tissue, the phase angle becomes negative, and the phase angle becomes more negative as the level of contact or coupling is increased. An example is shown in Table 1 for purposes of illustration.

TABLE 1

| Phase Angle Relation to Contact Conditions | |
|---|---|
| Phase Angle | Contact Condition |
| $\phi > -3°$ | little or no contact or coupling |
| $-3° < \phi < -7°$ | medium contact or coupling |
| $-7° < \phi < -10°$ | high contact or coupling |
| $\phi < -10°$ | excessive contact or coupling |

Figure 5:
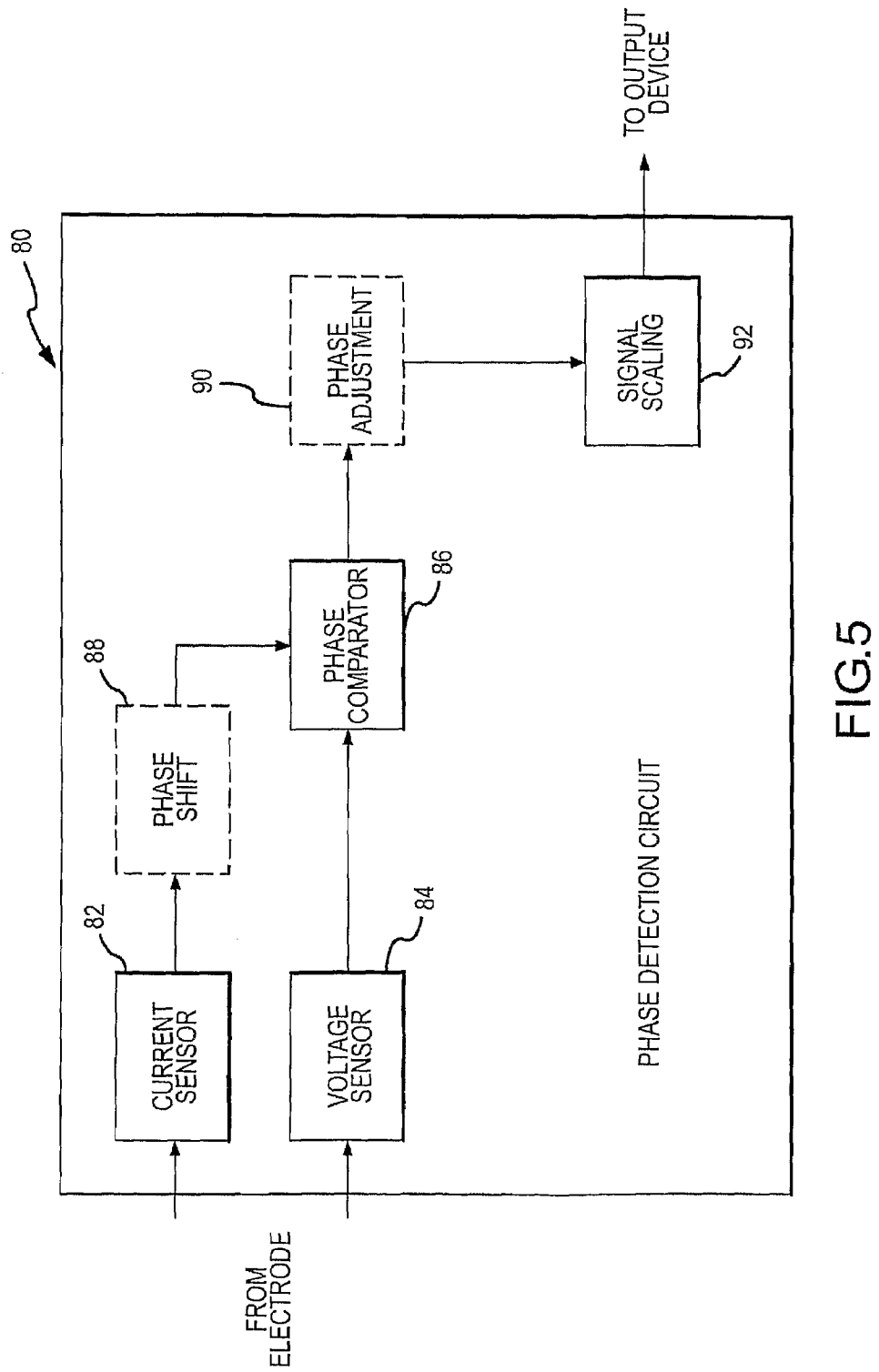
FIG. 5 is an exemplary phase detection circuit which may be implemented in the tissue ablation system for assessing electrode-tissue contact or coupling.

Although impedance measurements may be used to determine the phase angle, in an alternative embodiment, the measurement circuit 42 may be implemented as a phase detection circuit to directly determine the phase angle. An exemplary phase detection circuit 80 is shown in FIG. 5. Phase detection circuit 80 is shown and described with reference to functional components. It is noted that a particular hardware configuration is not necessary for a full understanding of the invention. Implementation of the phase detection circuit 80 in digital and/or analog hardware and/or software will be readily apparent to those having ordinary skill in the electronics art after becoming familiar with the teachings herein.

Exemplary phase detection circuit 80 may include a current sensor 82 and voltage sensor 84 for measuring current and voltage at the electrode-tissue interface. The current and voltage measurements may be input to a phase comparator 86. Phase comparator 86 provides a direct current (DC) output voltage proportional to the difference in phase between the voltage and current measurements.

In one embodiment, the current sensor 82 may be used to measure the ablation current. The sensor can be in series with ablation wire. For example, a Coilcraft CST1 current sensing transformer may be placed in series with the ablation wire. Alternatively, the current wire can pass through holes of a current sensor, with or without physical connection. In addition, the voltage between the ablation electrode and the ground patch can be sensed. This voltage can be attenuated so that it can be fed into a phase sensing circuit. The phase sensing circuit then measures the current and voltage and determines the phase angle between them, which is then correlated to a coupling level. In this way the ablation current can be used to measure the phase angle rather than injecting an additional current for the coupling sensing purpose.

Optionally, current measurements may be phase shifted by phase shift circuit 88 to facilitate operation of the phase comparator 86 by "correcting" phase lag between the measured current and the measured voltage. Also optionally, output from the phase comparator 86 may be "corrected" by phase adjustment circuit 90 to compensate for external factors, such as the type of grounding patch 46 being used. A signal scaling circuit 92 may also be provided to amplify the output (e.g., from milli-volts to volts) for use by various devices (e.g., the processor 50 and display device 54 in FIG. 3).

During ablation, the measured impedance, and its component's resistance and reactance, change with tissue temperature. In such conditions, the change due to changes in tissue temperature provides a measure of lesion formation during ablation.

It is noted that phase detection circuit 80 shown in FIG. 5 is provided as one example, and is not intended to be limiting. Other implementations may also be readily provided by those having ordinary skill in the electronics arts after becoming familiar with the teachings herein without departing from the scope of the invention.

Figure 6:
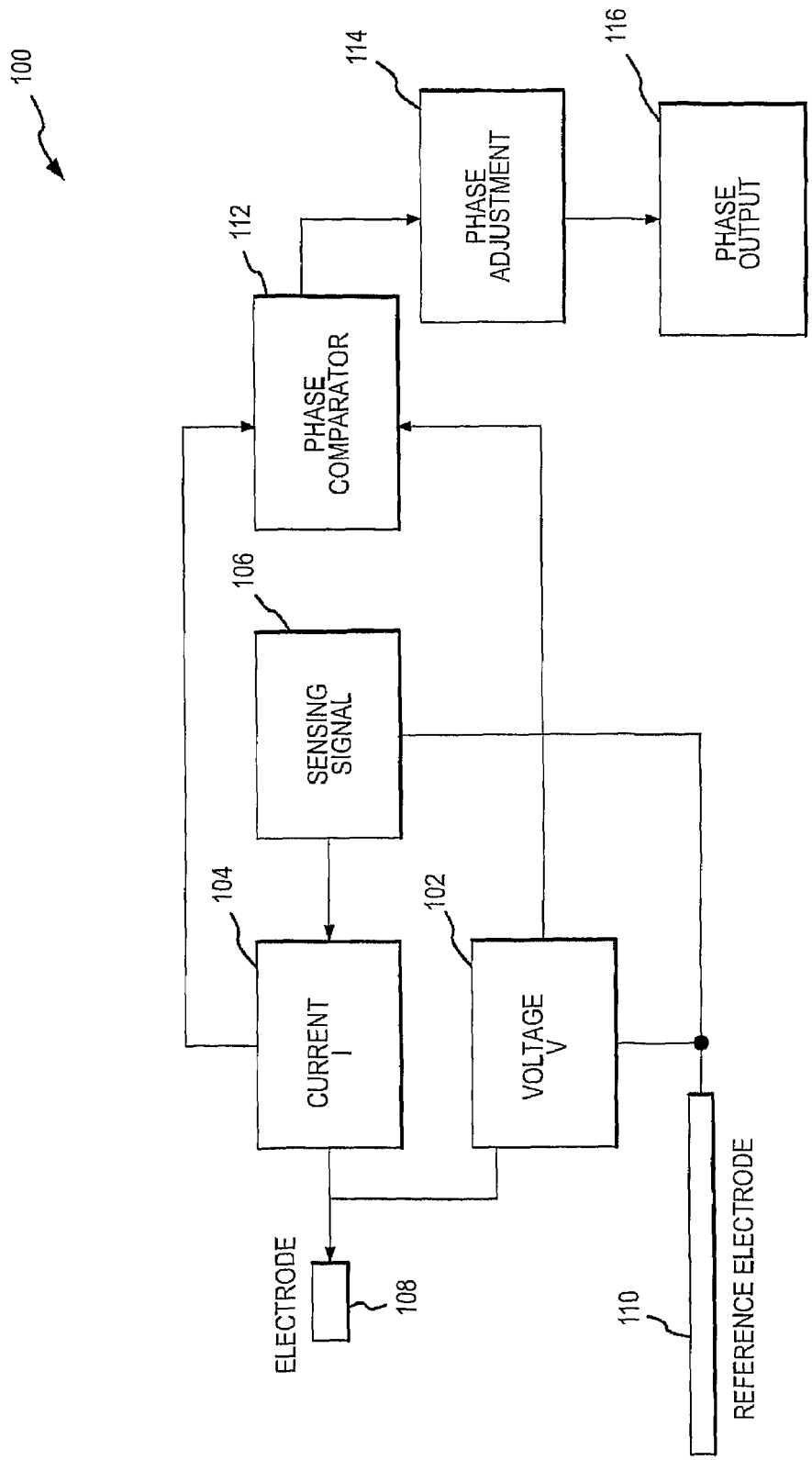
FIG. 6 is an exemplary block diagram showing phase angle measurement for contact sensing and tissue sensing.
Figure 7:
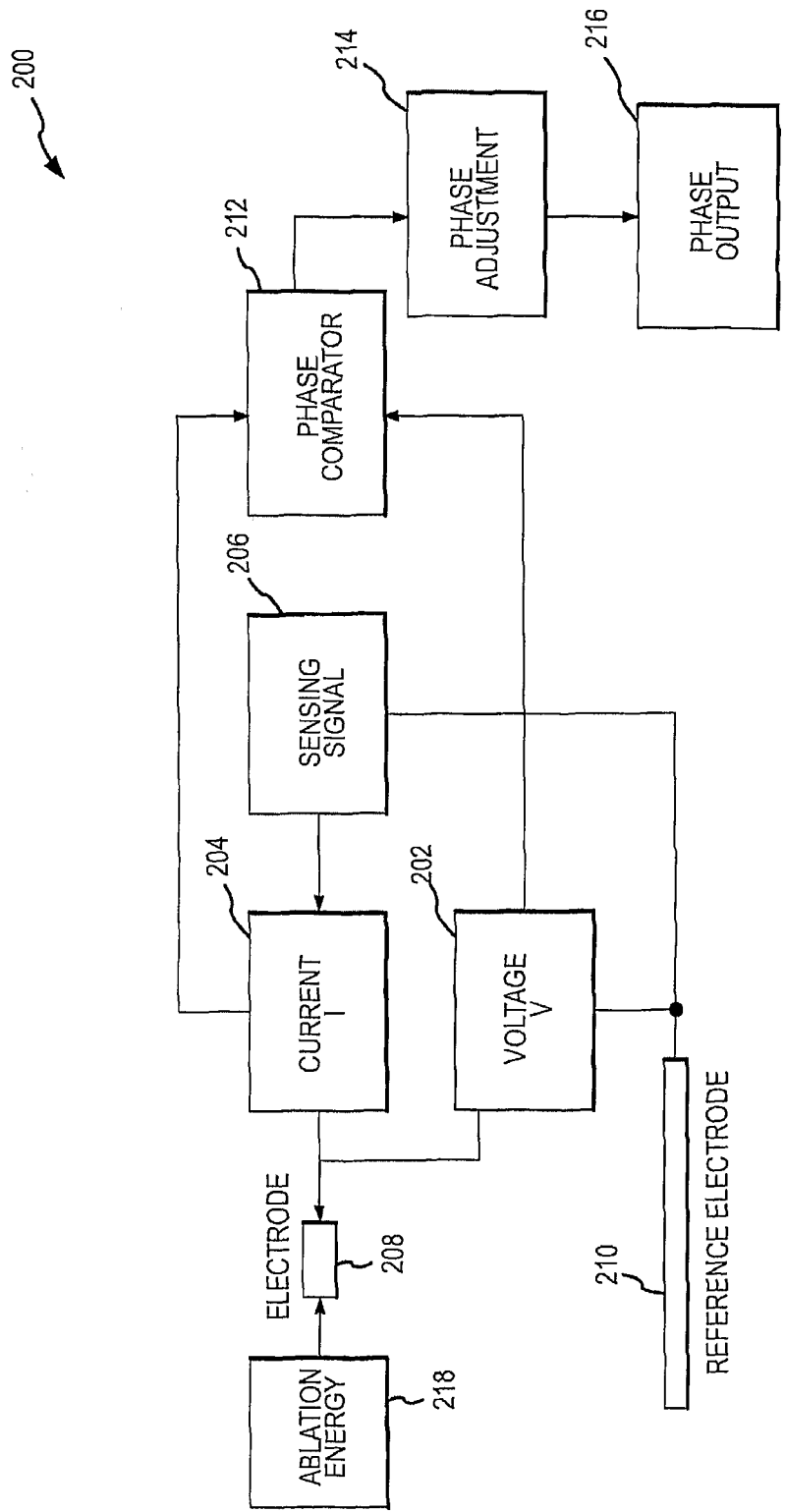
FIG. 7 is an exemplary block diagram showing phase angle measurement during ablation with both ablation energy and a contact sensing signal applied to the ablation electrode at the same time.
Figure 8:
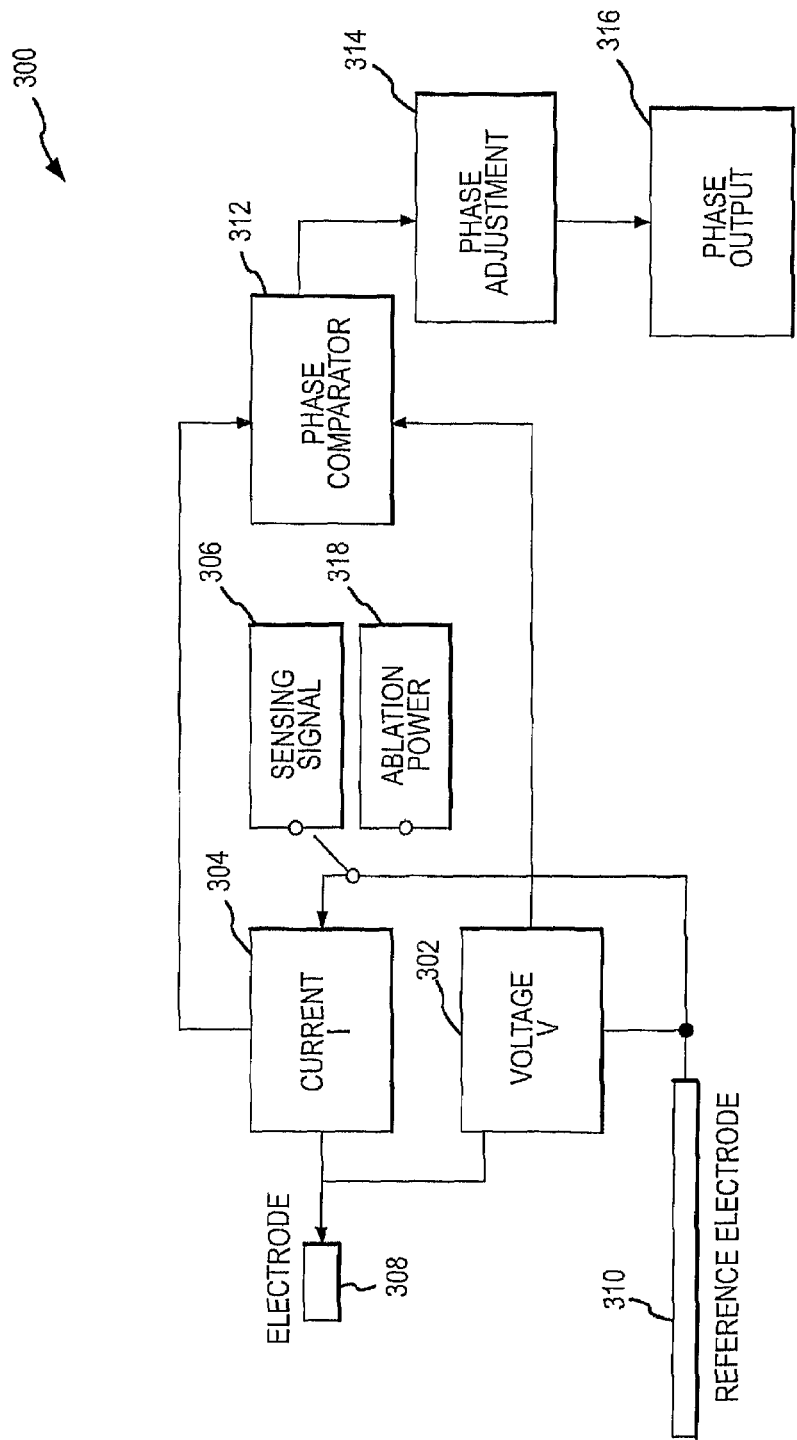
FIG. 8 is an exemplary block diagram showing phase angle measurement during ablation with switching between a sensing signal and ablation power.

Having described exemplary systems for electrode contact assessment, exemplary operational modes may now be better understood with reference to the block diagrams shown in FIG. 6-8. FIG. 6 is an exemplary block diagram 100 showing phase angle measurement for sensing contact or coupling. FIG. 7 is an exemplary block 200 diagram showing phase angle measurement during ablation with both ablation energy and a contact sensing signal applied to the ablation electrode at the same time. FIG. 8 is an exemplary block diagram 300 showing phase angle measurement during ablation with switching between sensing signal and ablation power. It is noted that 200-series and 300-series reference numbers are used in FIG. 7 and FIG. 8, respectively, to denote similar elements and these elements may not be described again with reference to FIG. 7 and FIG. 8.

As noted above, the phase angle method of sensing contact or coupling is based on the fact that (1) tissue is both more resistive and capacitive than blood, and (2) measured electrode impedance is mostly dependant on the immediate surrounding materials. Thus, when an electrode moves from blood to myocardium, the measured impedance value increases and phase angles change from 0° to negative values (capacitive). Phase angle may be used to represent the contact or coupling levels because phase angle is a relative term of both resistance and reactance. That is, it provides a 0° base line when the electrode is in contact with blood, and becomes increasingly more negative as more contact or coupling is established. It also minimizes the influence of the catheter, instrumentation, and physiological variables.

The phase angle measurement may be made by sampling both electrical voltage (V) 102 and current (I) 104 of a load and calculating the lag between those signals as the phase angle. As shown in FIG. 6, a sensing signal 106 is applied between the ablation electrode 108 and a reference electrode 110. This sensing signal 106 can, for example, be between 50 to 500 kHz at a small amplitude (<1 mA).

Exemplary instruments may be operated as frequencies of, for example but not limited to, 100 kHz, 400 kHz and 485 kHz, depending on the reference electrode configuration. Both current 104 and voltage 102 are sensed. These two signals are transmitted to a phase comparator 112 to calculate phase angle, which corresponds to the contact or coupling condition of the electrode 108. The raw phase angle signal is adjusted in block 114 to compensate for external influence on the phase angle, e.g., caused by the catheter, instrumentation, and physiological variables. It is also conditioned for easy interpretation and interface and then output in block 116 to other equipments for display or further processing.

The phase compensation may be achieved at the beginning of an ablation procedure. First, the catheter electrode is maneuvered to the middle of the heart chamber (e.g., the right atrium or left atrium) so that the electrode 108 only contacts blood. The system measures the phase angle and uses this value as a baseline for zero contact level. This adjustment compensates the fixed phase angles caused by catheter and patient such as catheter wiring, location of the reference electrode and skin or adiposity if external patch is used.

After the initial zero adjustment, the user may maneuver the catheter electrode to one or more desired sites to ablate arrhythmic myocardium. In an exemplary embodiment, the phase angle starts to change when the electrode 108 approaches to say within 3 mm from the myocardium and becomes increasingly more negative as more contact or coupling is established. The user may judge the quality of electrode contact or coupling before administering the ablation energy based on phase angle output. In an exemplary embodiment, this phase angle value is about −3° when a 4 mm ablation electrode actually contacts the myocardium. It is noted that there are at least two methods to measure phase angle during ablation, as described in more detail now with reference to FIG. 7 and FIG. 8.

In FIG. 7, ablation power 218 is applied to the electrode 208 while the sensing signal 206 is applied as well. The ablation and contact sensing operate at different frequencies. Accordingly, with filtering, the phase angle can be measured during ablation without disturbing the ablation of the myocardium.

Another option is to switch the phase measurement between the sensing signal 306 and ablation power 318, as indicated by switch 320 in FIG. 8. When the ablation power 318 is switched off during approach, the small amplitude sensing signal 306 is switched on and used to measure phase angle for sensing contact or coupling. When the ablation power 318 is switched on for the ablation procedure, the voltage and current of the large amplitude ablation power 318 are sensed and used as the contact or coupling indicator during ablation.

Figure 9A:
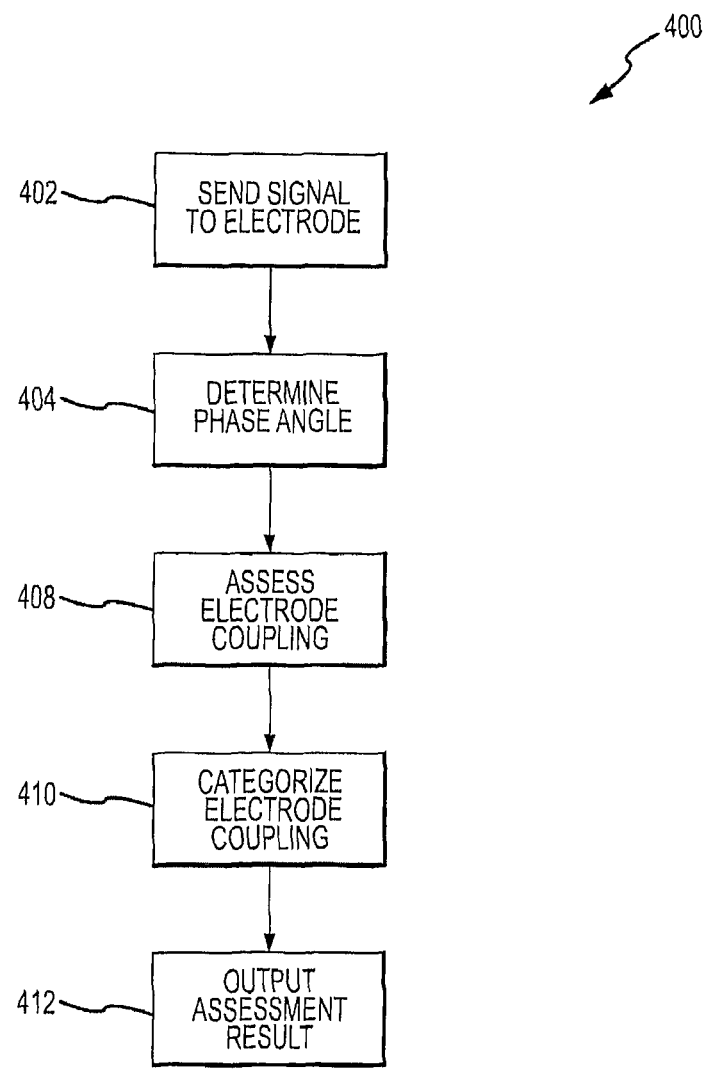
FIG. 9a illustrates one embodiment of a protocol that may be used to assess a coupling between an electrode and tissue based upon a phase angle comparison.

FIG. 9a illustrates one embodiment of an electrode coupling assessment protocol 400 (hereafter "assessment protocol 400") that may be used to assess the coupling of an electrode (e.g., a catheter electrode) with any appropriate tissue, where this assessment is phase angle based. Therefore, the protocol 400 may be used in relation to the embodiments discussed above in relation to FIGS. 6-8. In any case, "coupling" may include an electrical coupling of an electrode with a target tissue, a mechanical coupling between an electrode and the target tissue, or both.

Step 402 of the assessment protocol 400 of FIG. 9a is directed to sending an electrical signal to an electrode. Typically this will be after the electrode has been positioned at least in the general vicinity of the target tissue (e.g., within a heart chamber, such as the left atrium). A phase angle is thereafter determined at step 404, and the electrode coupling is thereafter assessed at step 408 based upon this phase angle. The electrode coupling assessment from step 408 may be categorized through execution of step 410. However, the categorization of step 410 may not be required in all instances. In any case, the result of the assessment from step 408 is output pursuant to step 412.

The electrical signal that is sent pursuant to step 402 of the protocol 400 may be at any appropriate frequency. However, only a single frequency is required to make the assessment for purposes of the protocol 400. The phase angle associated with step 404 may be the phase angle of the impedance. This phase angle may be determined in any appropriate manner, for instance using a phase sensing circuit of any appropriate configuration. In one embodiment and using the electrical signal associated with step 402, the phase angle is determined by measuring the current at the electrode, measuring the voltage between the electrode and another electrode (e.g., a return electrode), and then determining the phase angle between these current and voltage measurements. Another option would be to measure/determine the reactance and impedance in an appropriate manner, and to then determine the phase angle from these values (e.g., the sine of the phase angle being the ratio of the reactance to the impedance).

The phase angle may be determined using an RCL meter or a phase detection circuit (e.g., having an oscillator, multiplexer, filter, phase detection circuit), and may be referred to as a phase module. This phase module (measurement and/or detection) may be disposed at any appropriate location, such as by being incorporated into or embedded in the catheter handle set, by being in the form of a standalone unit between the ablation catheter and the power generator, by being incorporated into or embedded in the power generator, by being incorporated into an electrophysiology or EP mapping system, or by being part of an electrophysiology recording system.

Assessment of the coupling of the electrode with the tissue (step 408 of the protocol 400) may be undertaken in any appropriate manner. For instance, the phase angle determined through step 404 may be compared with one or more benchmark phase angle values (e.g., using a phase angle comparator). These benchmark phase angle values may be determined/set in any appropriate manner, for instance empirically. These benchmark phase angle values may be stored in an appropriate data structure, for instance on a computer-readable data storage medium, or otherwise may be made available to a phase angle comparator. Generally and in one embodiment, the phase angle decreases as more electrode-tissue (e.g., myocardium) coupling exists.

There may be one or more benchmark phase angle values (e.g., a single benchmark phase angle value or a range of benchmark phase angle values) for one or more of the following conditions for purposes of the categorization of step 410 of the assessment protocol 400 of FIG. 9a: 1) insufficient electrode coupling (e.g., an electrode coupling where the associated phase angle being less than "A" is equated with an insufficient electrode coupling); 2) sufficient electrode coupling (e.g., an electrode coupling with an associated phase angle greater than "A" and less than "B" being equated with a sufficient electrode coupling); and 3) elevated or excessive electrode coupling (e.g., an electrode coupling where the associated phase angle being greater than "B" is equated with an elevated or excessive electrode coupling). One embodiment equates the following phase angle values with the noted conditions:

insufficient electrode coupling: $\Phi > -5°$
sufficient electrode coupling: $-5° > \Phi > -10°$
elevated/excessive electrode coupling: $\Phi < -10°$ An "elevated" or "excessive" electrode coupling may be elevated/excessive in relation to the electrical coupling, the mechanical coupling, or both (the coupling between the electrode and the target tissue). In one embodiment, an elevated/excessive or hard electrode coupling means an elevated/excessive mechanical contact between the electrode and the target tissue. It may be desirable to know when an elevated or excessive mechanical contact exists between the electrode and tissue for a variety of reasons. For instance, it may be desirable to avoid an elevated or excessive mechanical contact between the electrode and the target tissue (e.g., to reduce the likelihood of directing the electrode through a tissue wall, membrane, or the like). However, it may also be desirable to know when a sufficient mechanical force is being exerted on the target tissue by the electrode (e.g., to increase the likelihood of directing the electrode through a tissue wall, membrane, or the like to gain access to a desired region on the other side of this tissue wall or membrane).

The result of the assessment of step 408 may be output in any appropriate manner pursuant to step 412 of the electrode coupling assessment protocol 400 of FIG. 9a. Any appropriate output may be utilized, for instance visually (e.g., a bar graph or any other appropriate display at any appropriate location or combination of locations), audibly (e.g., an alarm), physically (e.g., by vibrating a handle being held by a physician that is performing an electrode-based procedure, and as discussed in more detail herein), or any combination thereof. A single output may be provided. A combination of two or more outputs may also be utilized. One or more outputs may be issued to a single location or to multiple locations.

Figure 9B:
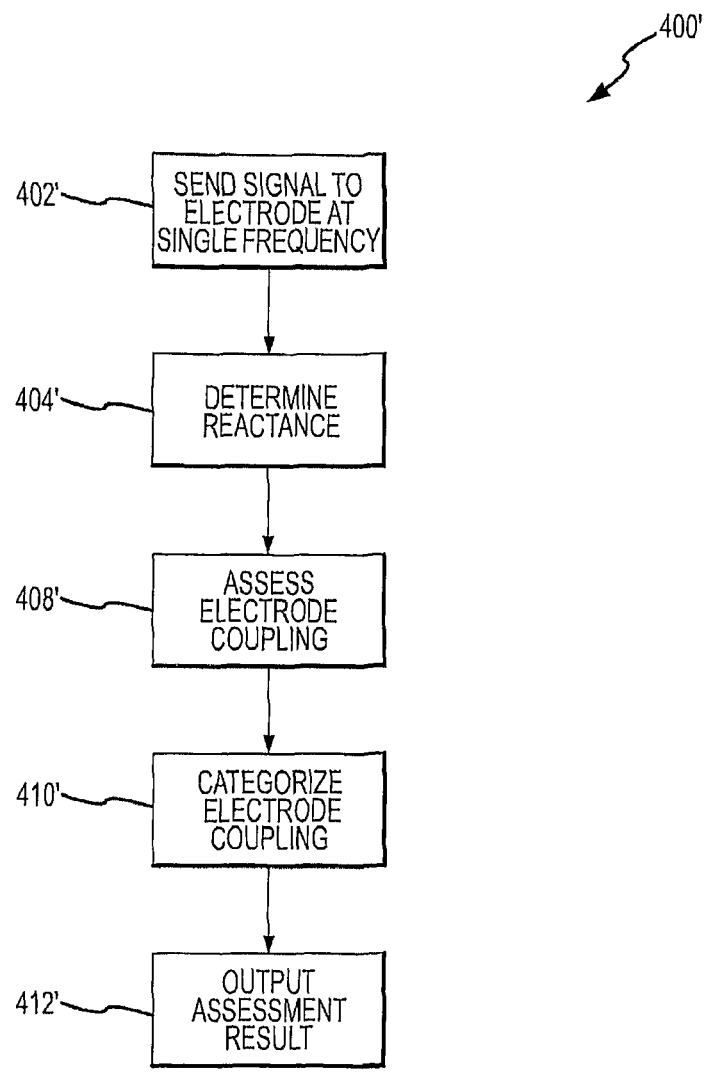
FIG. 9b illustrates one embodiment of a protocol that may be used to assess a coupling between an electrode and tissue based upon a reactance comparison.

FIG. 9b illustrates one embodiment of an electrode coupling assessment protocol 400' that may be used to assess the coupling of an electrode (e.g., a catheter electrode) with any appropriate tissue, where this assessment is reactance based. As the protocol 400' is a variation of the protocol 400 of FIG. 9a, a "single prime" designation is used in relation the reference numerals that identify the individual steps of the protocol 400' of FIG. 9b.

Step 402' of the assessment protocol 400' of FIG. 9b is directed to sending an electrical signal. Only a single frequency is required for the protocol 400' to provide its assessment. That is, the electrode coupling assessment may be provided using a single frequency in the case of the assessment protocol 400'. Typically this will be after the electrode has been positioned at least in the general vicinity of the target tissue (e.g., within a heart chamber). A reactance of the electrical circuit that includes the electrode and the target tissue is thereafter determined at step 404'. This reactance may be determined in any appropriate manner. For instance, the phase angle may be measured (e.g., in accordance with the foregoing), the impedance may be measured, and the reactance may be calculated from these two values (e.g., the sine of the phase angle is equal to the ratio of the reactance to the impedance). Another option for determining the reactance would be to determine the phase or frequency response of a pulse wave.

The electrode coupling is assessed at step 408' of the protocol 400' based upon the above-noted reactance. This electrode coupling from step 408' may be categorized through execution of step 410'. However, the categorization of step 410' may not be required in all instances. In any case, the result of the assessment is output pursuant to step 412'. Step 412' may correspond with step 412 of the electrode coupling assessment protocol 400 of FIG. 9*a*.

Assessment of the electrode coupling with the tissue (step 408' of the protocol 400') may be undertaken in any appropriate manner. For instance, the reactance determined through step 404' may be compared with one or more benchmark reactance values (e.g., using a reactance comparator). These benchmark reactance values may be determined/set in any appropriate manner, for instance empirically. These benchmark reactance values may be stored in an appropriate data structure, for instance a computer-readable data storage medium, or otherwise may be made available to a reactance comparator. Generally and in one embodiment, the reactance decreases as more electrode-tissue (e.g., myocardium) coupling exists.

There may be one or more benchmark reactance values (e.g., a single benchmark reactance value or a range of benchmark reactance values) for one or more of the following conditions for purposes of the categorization of step 410': 1) insufficient electrode coupling (e.g., an electrode coupling where the associated reactance being less than "A" is equated with insufficient electrode coupling); 2) sufficient electrode coupling (e.g., an electrode coupling with an associated reactance greater than "A" and less than "B" being equated with a sufficient electrode coupling); and 3) elevated or excessive electrode coupling (e.g., an electrode coupling where the associated reactance being greater than "B" is equated with an elevated or excessive electrode coupling). One embodiment equates the following reactance values for the noted conditions:

insufficient electrode coupling: X>−5
sufficient electrode coupling: −5>X>−15
elevated/excessive electrode coupling: X<−15

Figure 9C:
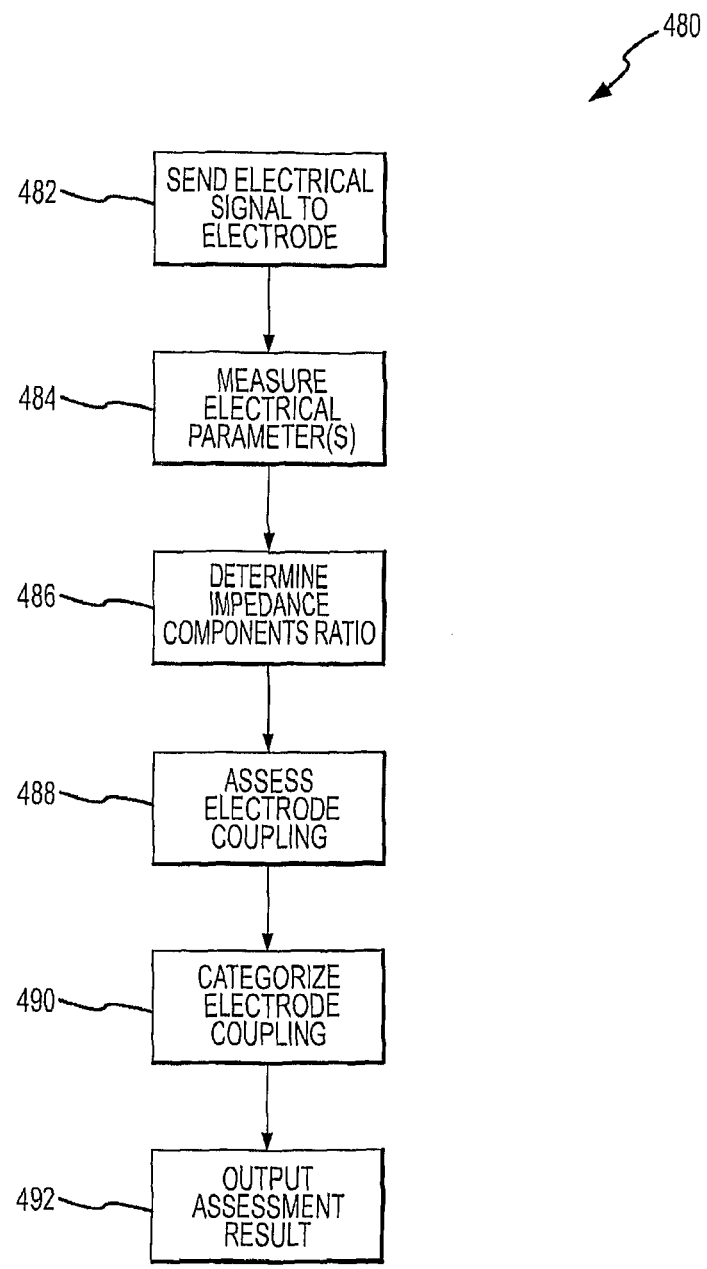
FIG. 9c illustrates one embodiment of a protocol that may be used to assess a coupling between an electrode and tissue based upon an impedance components ratio comparison.

One benefit of basing the electrode coupling assessment upon phase angle is that the phase angle is more insensitive to changes from patient to patient, or operation setup, than both impedance or reactance when considered alone or individually. Other ways of realizing less sensitivity to changes from tissue to tissue or such other conditions may be utilized to provide an electrode coupling assessment. FIG. 9*c* illustrates such an embodiment of an electrode coupling assessment protocol 480—a protocol 480 that may be used to assess the coupling of an electrode (e.g., a catheter electrode) with any appropriate tissue. Step 482 of the assessment protocol 480 is directed to sending an electrical signal to an electrode at a certain frequency. At least one electrical parameter is measured at step 484. What may be characterized as an "impedance components ratio" is then determined from this measurement at step 486. The phrase "impedance components ratio" means any term that is a ratio of two individual components of the impedance, such as the phase angle (the tangent of the phase angle being equal to the ratio of reactance to resistance). The impedance components ratio may be determined in any appropriate manner, such as by simply measuring a phase angle. Other ways for determining the impedance components ratio include without limitation determining a resistance and reactance at the frequency encompassed by step 482, and calculating the impedance components ratio from these two parameters. Using a ratio of two components that relate to impedance may provide less sensitivity to changes from tissue to tissue for an electrode coupling assessment—an assessment of the coupling between an electrode and the target tissue.

The electrode coupling is assessed at step 488 of the protocol 480. This electrode coupling from step 488 may be categorized through execution of step 490, where step 490 may be in accordance with step 410 of the electrode coupling assessment protocol 400 discussed above in relation to FIG. 9*a*. As such, the categorization of step 490 may not be required in all instances. In any case, the result of the assessment is output pursuant to step 492. Step 492 may be in accordance step 412 of the electrode coupling assessment protocol 400 discussed above in relation to FIG. 9*a*.

Figure 10:
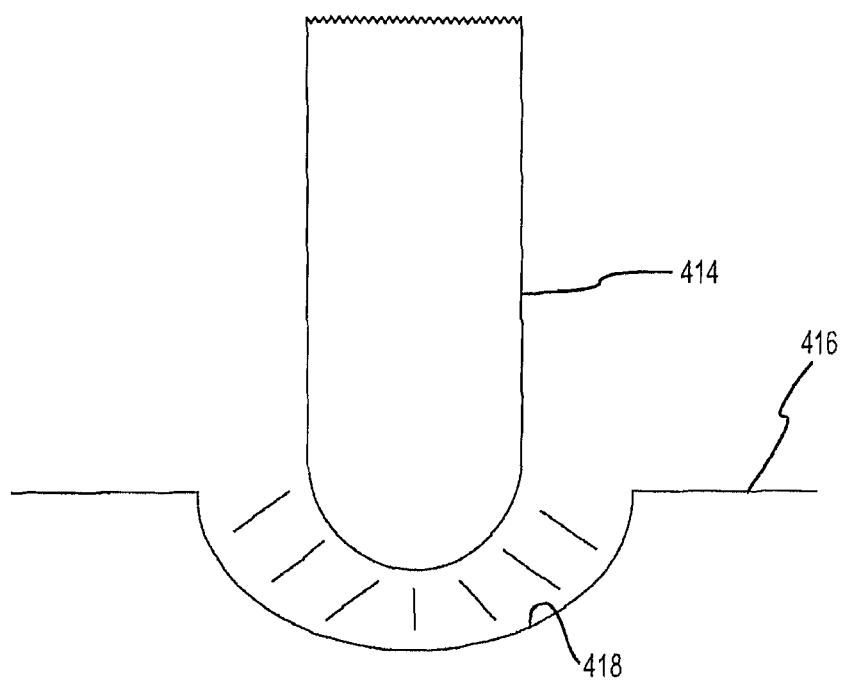
FIG. 10 illustrates a representative, schematic representation of an electrical coupling between an electrode and tissue.

Each of the protocols of FIGS. 9*a-c* encompasses the electrode coupling being a mechanical coupling between the electrode and the target tissue (i.e., physical contact), as well as an electrical coupling (e.g., a condition when a sufficient portion of the electrical energy passes from the electrode to the target tissue). Any time there is a mechanical coupling, there is an electrical coupling. The reverse, however, is not true. There may be an electrical coupling without the electrode being in contact with the target tissue. FIG. 10 illustrates a representative example of where there is an electrical coupling without having mechanical contact between an electrode 414 and the target tissue 416. Here, the electrode 414 is disposed within a cavity 418 on the surface of the tissue 416, and which provides an electrical coupling between the electrode 414 and the target tissue 416. Therefore, each of the protocols of FIGS. 9*a-c* may provide an indication of electrical coupling without requiring mechanical contact between the electrode and the target tissue.

Figure 11A:
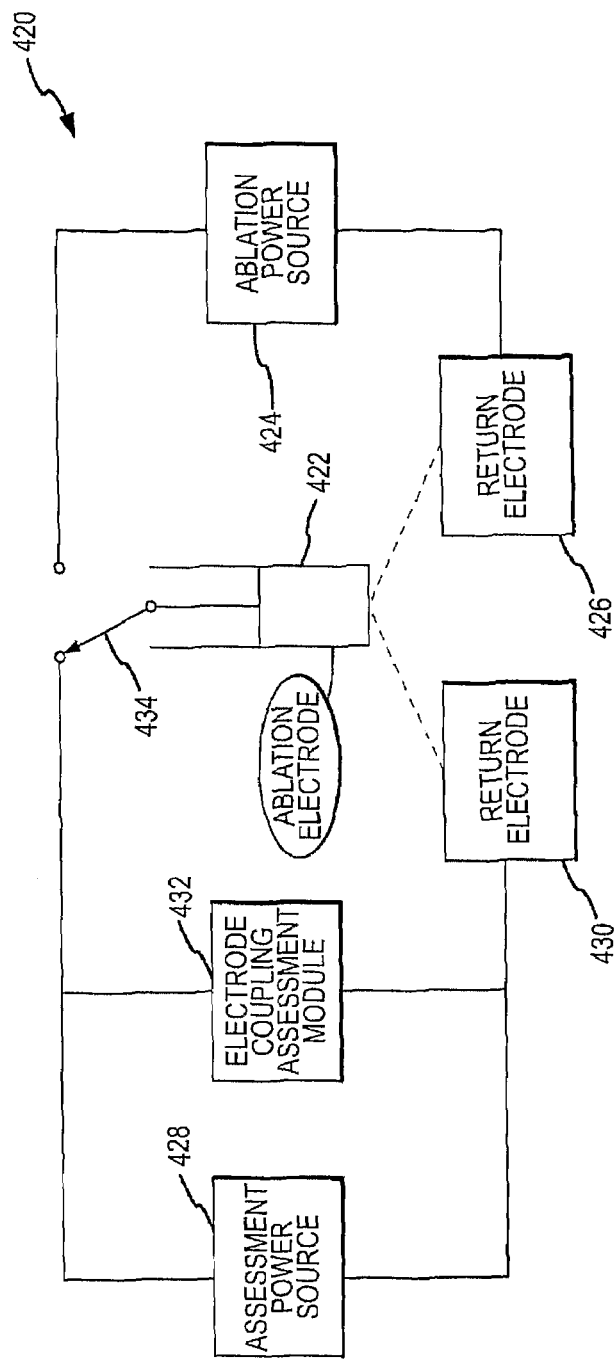
FIG. 11a illustrates a schematic of one embodiment of an ablation system that uses two power sources operating at different frequencies, where only one of these power sources is interconnected with the ablation electrode at any one time, and where one of these power sources is used for assessing a coupling between an electrode and tissue.
Figure 11B:
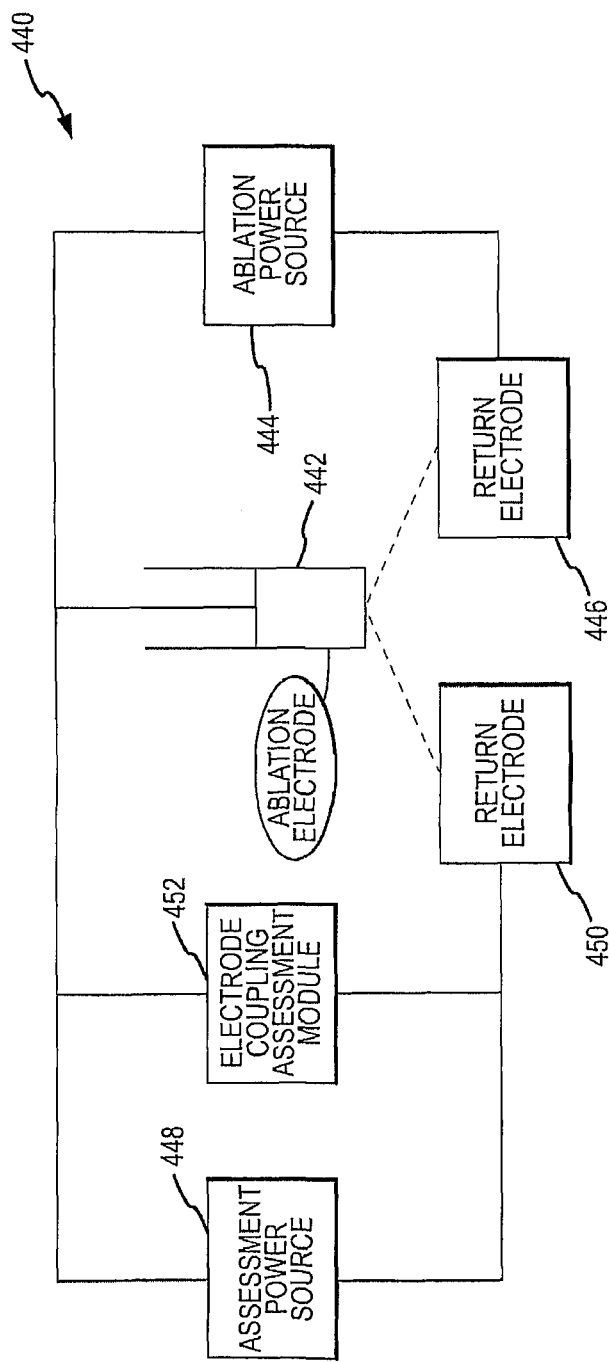
FIG. 11b illustrates a schematic of one embodiment of an ablation system that uses two power sources operating at different frequencies, where both power sources are always interconnected with the ablation electrode, and where one of these power sources is used for assessing a coupling between an electrode and tissue.
Figure 11C:
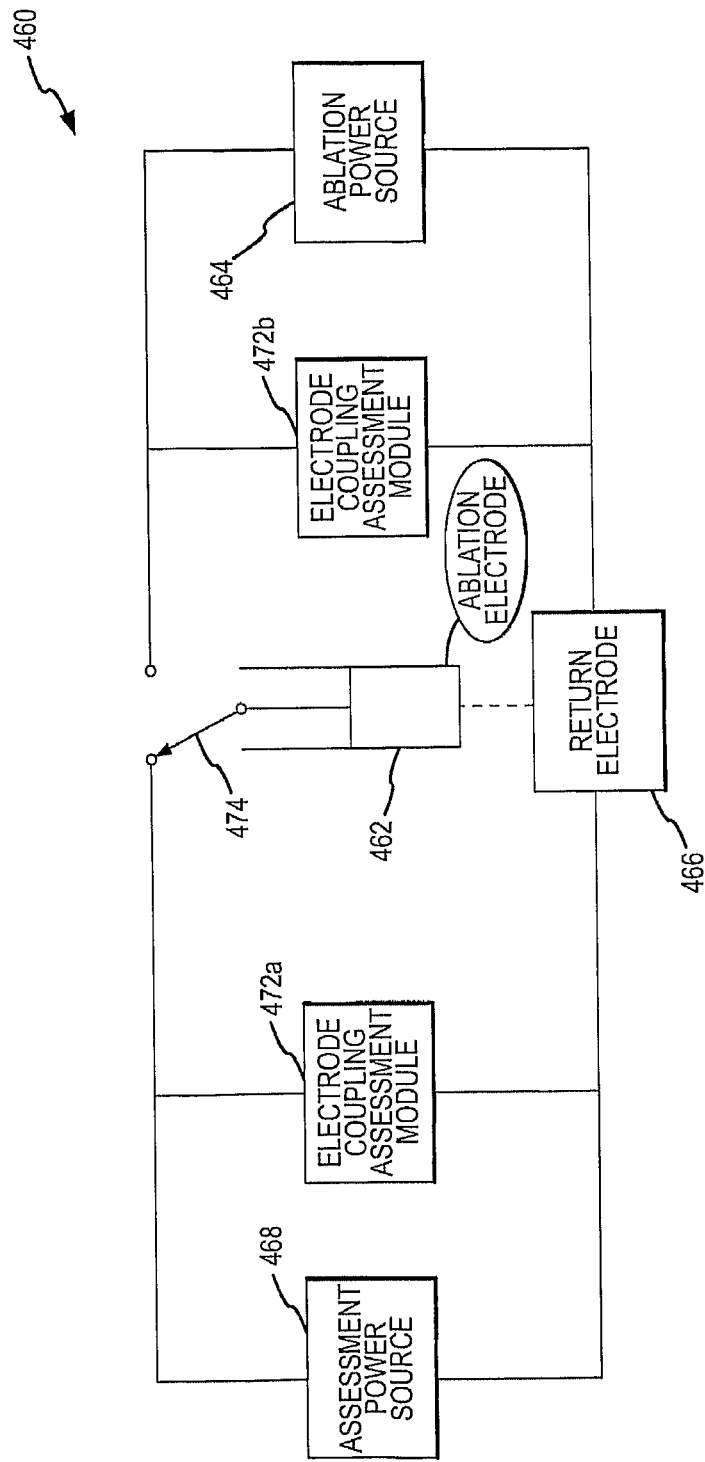
FIG. 11c illustrates a schematic of one embodiment of an ablation system that uses two power sources operating at least generally at the same frequency, where only one of these power sources is interconnected with the ablation electrode at any one time, and where each of these power sources may be used for assessing a coupling between an electrode and tissue.

FIGS. 11*a-c* schematically present various configurations that may be used in relation to providing an electrode coupling assessment. Although each of these systems will be discussed in relation to an ablation electrode, this electrode coupling assessment may be used for any appropriate application where an electrode provides any appropriate function or combination of functions. Each of the systems of FIGS. 11*a-c* may be used to provide the assessment protocols discussed above in relation to FIGS. 9*a-c*. It should also be appreciated that it may be desirable to utilize various other components to commercially implement these configurations, such as filters (e.g., as there may be a current from one or more other sources that should be isolated from the current being used to make the coupling assessment), one or more components to "electrically protect" the patient and/or the electrical circuitry used to make the electrode coupling assessment.

FIG. 11*a* illustrates an ablation system 420 that includes an ablation power source 424, an ablation electrode 422, and a return electrode 426. Any appropriate frequency may be used by the ablation power source 424. Each of the ablation electrode 422 and return electrode 426 may be of any appropriate size, shape, and/or configuration. Typically the ablation electrode 422 will be in the form of a catheter electrode that is disposed within the patient's body. The return electrode 426 may be disposed at any appropriate location (e.g., a ground patch disposed on the skin of a patient; a catheter electrode disposed within the body of a patient).

Additional components of the ablation system 420 include an electrode coupling assessment power source 428 (hereafter the "assessment power source 428"), an assessment return electrode 430, and an electrode coupling assessment module 432 (hereafter the "assessment module 432"). Any appropriate frequency may be used by the assessment power source 428. Typically, the ablation power source 424 will also use a significantly higher current than the assessment power source 428.

The assessment return electrode 430 may be of any appropriate size, shape, and/or configuration, and may be disposed at any appropriate location. One embodiment has the return electrode 426 and the assessment return electrode 430 being in the form of separate structures that are disposed at different locations. Another embodiment has the functionality of the return electrode 426 and the functionality of the assessment return electrode 430 be provided by a single structure (a single unit that functions as both a return electrode 426 and as an assessment return electrode 430).

The ablation electrode 422 either receives power from the ablation power source 424 or the assessment power source 428, depending upon the position of a switch 434 for the ablation system 420. That is, ablation operations and electrode coupling assessment operations may not be simultaneously conducted in the case of the ablation system 420 of FIG. 11*a*. During electrode coupling assessment operations, the switch 434 is of course positioned to receive power from the assessment power source 428. This allows the assessment module 432 to assess the coupling between the ablation electrode 422 and the target tissue. Any appropriate configuration may be utilized by the assessment module 432 to provides its electrode coupling assessment function, including without limitation the various configurations addressed herein (e.g., assessment based upon phase angle comparisons; assessment based upon reactance comparisons; assessment based upon impedance components ratio comparisons; assessment based upon identifying the frequency associated with a 0° phase frequency or a 0 inductance frequency as will be discussed below in relation to FIGS. 12*a*-*b*). The assessment module 432 may provide the electrode coupling assessment using any of the protocols of FIGS. 9*a*-*c* from a single frequency.

FIG. 11*b* illustrates an ablation system 440 that includes an ablation power source 444, an ablation electrode 442, and a return electrode 446. Any appropriate frequency may be used by the ablation power source 444. Each of the ablation electrode 442 and return electrode 446 may be of any appropriate size, shape, and/or configuration. Typically the ablation electrode 442 will be in the form of a catheter electrode that is disposed within the patient's body. The return electrode 446 may be disposed at any appropriate location (e.g., a ground patch disposed on the skin of a patient; a catheter electrode disposed within the body of a patient).

Additional components of the ablation system 440 include an electrode coupling assessment power source 448 (hereafter the "assessment power source 448"), an assessment return electrode 450, and an electrode coupling assessment module 452 (hereafter the "assessment module 452"). Any appropriate frequency may be used by the assessment power source 448. However, the ablation power source 444 and the assessment power source 448 operate at different frequencies in the case of the ablation system 440 in order to accommodate the simultaneous execution of ablation and electrode coupling assessment operations. Moreover, typically the ablation power source 444 will also use a significantly higher current than the assessment power source 448.

The assessment return electrode 450 may be of any appropriate size, shape, and/or configuration, and may be disposed at any appropriate location. One embodiment has the return electrode 446 and the assessment return electrode 450 being in the form of separate structures that are disposed at different locations. Another embodiment has the functionality of the return electrode 446 and the functionality of the assessment return electrode 450 be provided by a single structure (a single unit that functions as both a return electrode 446 and as an assessment return electrode 450).

The ablation electrode 442 may simultaneously receive power from the ablation power source 444 and the assessment power source 448. That is, ablation operations and electrode coupling assessment operations may be simultaneously executed in the case of the ablation system 440 of FIG. 11*b*. In this regard, the ablation power source 444 and the assessment power source 448 again will operate at different frequencies. The assessment module 452 may provide the electrode coupling assessment using any of the protocols of FIGS. 9*a*-*c* from a single frequency. In any case, the assessment module 452 assesses the coupling between the ablation electrode 442 and the target tissue. The discussion presented above with regard to the assessment module 432 for the ablation system 420 of FIG. 11*a* is equally applicable to the assessment module 452 for the ablation system 440 of FIG. 11*b*.

FIG. 11*c* illustrates an ablation system 460 that includes an ablation power source 464, an ablation electrode 462, and a return electrode 466. Any appropriate frequency may be used by the ablation power source 464. Each of the ablation electrode 462 and return electrode 466 may be of any appropriate size, shape, and/or configuration. Typically the ablation electrode 462 will be in the form of a catheter electrode that is disposed within the patient's body. The return electrode 466 may be disposed at any appropriate location (e.g., a ground patch disposed on the skin of a patient; a catheter electrode disposed within the body of a patient).

Additional components of the ablation system 460 include an electrode coupling assessment power source 468 (hereafter the "assessment power source 468"). Any appropriate frequency may be used by the assessment power source 468. Typically, the ablation power source 464 will also use a significantly higher current than the assessment power source 468.

The ablation system 460 further includes a pair of electrode coupling assessment modules 472*a*, 472*b* (hereafter the "assessment module 472*a*" and "the assessment module 472*b*"). The assessment module 472*a* is associated with the assessment power source 468, while the assessment module 472*b* is associated with the ablation power source 464. Both ablation operations and electrode coupling assessment operations utilize the return electrode 466 in the illustrated embodiment, although it may be possible to utilize separate return electrodes as in the case of the embodiments of FIGS. 11*a* and 11*b* discussed above.

The ablation electrode 462 either receives power from the ablation power source 464 or the assessment power source 468, depending upon the position of a switch 474 for the ablation system 460. However, electrode coupling assessment operations may be executed regardless of the position of the switch 474, unlike the embodiment of FIG. 11*a*. When the ablation electrode 462 is electrically interconnected with the assessment power source 468 through the switch 474, the assessment module 472*a* is used to assess the coupling between the ablation electrode 462 and the target tissue. When the ablation electrode 462 is electrically interconnected with the ablation power source 464 through the switch 474, the assessment module 472*b* is used to assess the coupling between the ablation electrode 462 and the target tissue. The assessment modules 427*a*, 472*b* may each provide an electrode coupling assessment using any of the protocols of FIGS. 9*a*-*c* from a single frequency.

Any appropriate configuration may be utilized by each of the assessment module 472*a*, 472*b* to provide their respective electrode coupling assessment functions, including without limitation the various configurations addressed herein. The discussion presented above with regard to the assessment module 432 for the ablation system 420 of FIG. 11*a* is equally applicable to the assessment modules 472*a*, 472*b* for the ablation system 460 of FIG. 11*c*. Typically, the assessment modules 472*a*, 472*b* will be of the same configuration for assessing electrode coupling, although such may not be required in all instances. When the assessment modules 472a, 472b are the same configuration, the ablation power source 464 and the assessment power source 468 will typically operate at the same frequency. Therefore, the ablation system 460 accommodates the assessment of electrode coupling prior to initiating ablation operations (e.g., using an assessment current and the assessment module 472a), and further accommodates the assessment of electrode coupling during ablation operations (e.g., using the actual ablation current versus a smaller current, and using the assessment module 472b). The ablation system 440 of FIG. 11b also accommodates the assessment of electrode coupling during ablation operations, but it uses a separate assessment current versus the actual ablation current.

One of the electrodes used by the assessment module in each of the embodiments of FIGS. 11a-c is of course the ablation or "active" electrode. Both the electrode coupling assessment module and the ablation electrode need another electrode that interfaces with the patient in some manner to provide their respective functions. FIG. 1a illustrates one embodiment where the return electrode used by the assessment module and the return electrode that cooperates with the ablation electrode to provide electrical energy to the tissue for providing one or more desired functions are integrated into a common structure. More specifically, an ablation electrode 20 (e.g., a catheter electrode) is disposed in a chamber of the heart 16 (e.g., the left atrium), and is in the form of a catheter electrode 20. A return electrode 20a (e.g., a catheter electrode) is also disposed in the same chamber of the heart 16 and may be used by each of the assessment modules of FIGS. 11a-c (to assess coupling of the ablation electrode 20 with the target tissue 24) and the ablation electrode 20 (to deliver electrical energy to the target tissue 24 to provide a desired medical function). Therefore, the ablation electrode 20 and the return electrode 20a may be associated with different catheters, and thereby may be independently moved or manipulated. In one embodiment, the return electrode 20a has a larger surface area than the ablation electrode 20. Each of the ablation electrode 20 and the return electrode 20a have electrode tips that are spaced from each other.

The configuration shown in FIG. 1a provides two electrodes 20, 20a in a common heart chamber. Another option would be to have two or more electrodes be associated with a common catheter, but where the catheter has two separated distal portions each with an electrode on a separate electrode tip on a distal end thereof such that the electrode tips are spaced from each other.

Figure 12A:
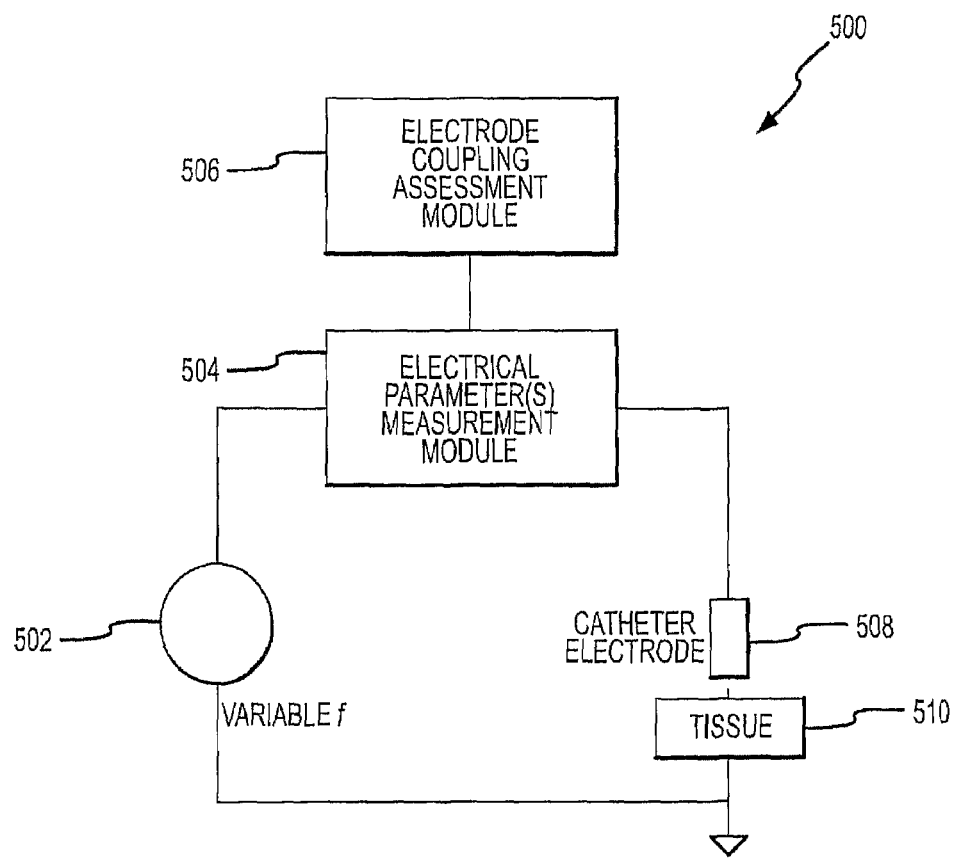
FIG. 12a illustrates one embodiment of a system for assessing a coupling between an electrode and tissue.
Figure 12B:
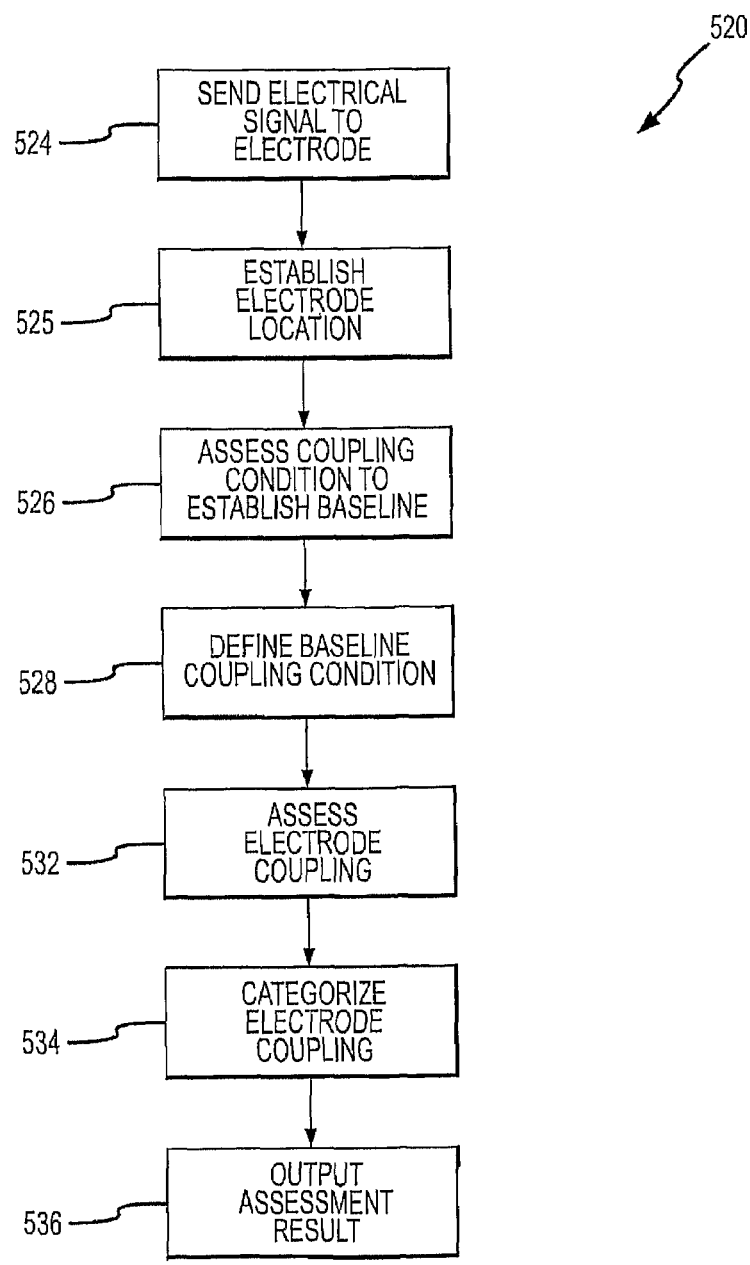
FIG. 12b illustrates one embodiment of a protocol that may be used to assess a coupling between an electrode and tissue based upon identifying a baseline coupling condition.

One or more ways of using a phase angle to assess the coupling between an active electrode and the target tissue have been presented above. Another way in which a phase angle may be used to assess electrode coupling is illustrated in FIGS. 12a-b. FIG. 12a presents a schematic of an electrode coupling assessment system 500 which includes a variable frequency source 502, an electrical parameter measurement module 504, an electrode coupling assessment module 506, and an electrode 508 that is to be coupled with tissue 510 to provide a desired function or combination of functions (e.g., ablation). The return electrode is not illustrated in FIG. 12a, but may be of any appropriate type and disposed at any appropriate location. Generally, the variable frequency source 502 provides an electrical signal to the electrode 508 for purposes of transmitting electrical energy to the tissue 510. The electrical parameter measurement module 504 may be of any appropriate type and/or configuration, measures one or more electrical parameters, and provides information used by the electrode coupling assessment module 506. The electrode coupling assessment module 506 assesses the coupling between the electrode 508 and the tissue 510.

FIG. 12b presents one embodiment of an electrode coupling protocol 520 that may be used by the electrode coupling assessment module 506 of FIG. 12a. One or more electrical signals are sent to the electrode 508 through execution of step 524. A baseline coupling condition can be assessed. For example, the baseline coupling condition can be defined pursuant to steps 524-528 of protocol 520. The term "baseline coupling condition" encompasses a zeroed phase angle or zeroed reactance at a desired frequency in a medium (e.g., blood).

A determination is made through execution of step 525 to determine when the electrode is in the desired medium, e.g., the blood. Next, through the execution of step 526, the baseline coupling condition is established. For example, the physician can activate an input device to indicate the establishment of the baseline coupling condition. Then protocol 520 adjusts to the baseline coupling condition in step 528 by correcting the phase angle or the reactance to zero.

In an alternative to zeroing the baseline coupling condition, the value(s) of the baseline coupling condition established in step 526 may be stored and used to determine an electrode coupling condition relative to such a baseline coupling condition.

In a second alternative, the baseline coupling condition may be determined by comparing the determined phase angle with one or more predetermined benchmark values. These benchmark values may be determined/set in any appropriate manner, for instance empirically through in vitro, ex vivo, or in vivo studies. These benchmark values may be stored in an appropriate data structure, for instance on a computer-readable data storage medium, or otherwise may be made available to a phase comparator.

The electrode coupling may be assessed pursuant to step 532 of the protocol 520 using the baseline coupling condition from step 528. One or more electrical parameters may be determined in any appropriate manner and compared with the corresponding value of the baseline coupling condition from step 528. For instance, the following categories may be provided: 1) insufficient electrode coupling (e.g., an electrode coupling where the value(s) associated with a baseline coupling condition being less than "A" is equated with insufficient electrode coupling); 2) sufficient electrode coupling (e.g., an electrode coupling where the value(s) associated with a baseline coupling condition greater than "A" and less than "B" is equated with a sufficient electrode coupling); and 3) elevated or excessive electrode coupling (e.g., an electrode coupling where the value(s) associated with a baseline coupling condition being greater than "B" is equated with an elevated or excessive electrode coupling).

Figure 12C:
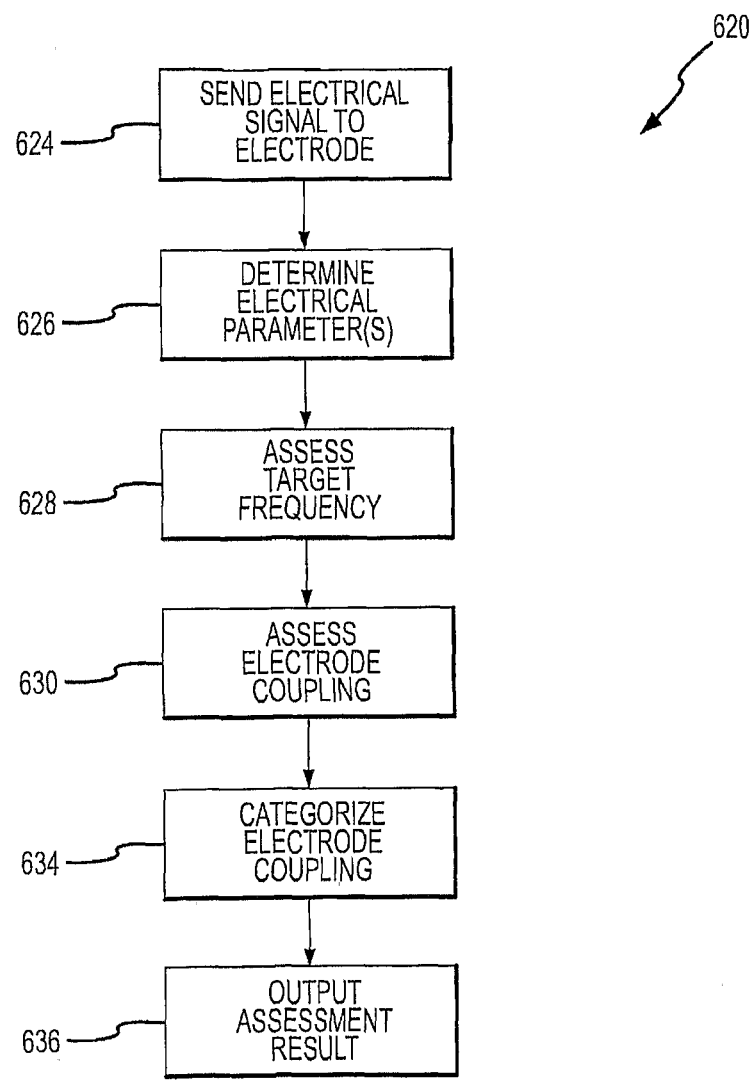
FIG. 12c illustrates one embodiment of a protocol that may be used to assess a coupling between an electrode and tissue based upon identifying a target frequency.

In another embodiment, the electrical coupling is measured as a function of a "target frequency"—a frequency that corresponds to a preset value for an electrical parameter (e.g., a preset reactance or a phase angle value). FIG. 12c presents one embodiment of an electrode coupling protocol 620 that may be used by the electrode coupling assessment module 506 of FIG. 12a. Electrical signals are sent to the electrode 508 through execution of step 624. The electrical signals are sent at varying frequencies. At each frequency sent, step 626 measures the reactance and/or phase. Step 628 compares the measured reactance or phase with a preset value. The frequency at which the reactance or phase matches the preset value is the "target frequency." Any appropriate value may be used for the preset value for purposes of step 628, including a positive value, zero, or a negative value (e.g., a zero phase angle, such that the target frequency may be referred to as a 0° phase frequency; or a zero inductance, such that the target condition frequency may be referred to as a 0 inductance frequency).

When the protocol 620 determines that the target frequency exists, the protocol 620 proceeds to step 630 where the coupling of the electrode 508 with the tissue 510 is assessed using the information provided by step 628, and the result of this assessment is output pursuant to step 636 of the protocol 620. Step 636 may be in accordance with step 412 of the protocol discussed above in relation to FIG. 9*a*.

Assessment of the electrode coupling with the tissue is provided through step 630 of the protocol 620 of FIG. 12*c*. The target frequency from step 628 may be compared with one or more benchmark frequency values (e.g., using a comparator). These benchmark frequency values may be determined/set in any appropriate manner. The values can be predetermined, for instance empirically through in vitro, ex vivo, or in vivo studies. These benchmark frequency values may be stored in an appropriate data structure, for instance on a computer-readable data storage medium. The benchmark frequency values can also be determined during the procedure by a physician. For example, a determination can be made when the electrode is in the desired medium, e.g., the blood. At that point the physician can activate an input device to set the benchmark value for the existing coupling relevant condition.

There may be one or more benchmark frequency values (e.g., a single benchmark frequency value or a range of benchmark frequency values) for one or more of the following conditions for purposes of the categorization for the assessment protocol 620 of FIG. 12*c*: 1) insufficient electrode coupling (e.g., an electrode coupling where the target frequency being less than "A" is equated with insufficient electrode coupling); 2) sufficient electrode coupling (e.g., an electrode coupling where the target frequency is greater than "A" and less than "B" is equated with sufficient electrode coupling); and 3) excessive electrode coupling (e.g., an electrode coupling where the target frequency being greater than "B" is equated with an excessive electrode coupling). One embodiment equates the following target frequency values for the noted conditions (where $F_t$ is the target frequency for the noted condition):

insufficient electrode coupling: $F_t$<120 kHz
sufficient electrode coupling: 120 kHz<$F_t$<400 kHz
elevated/excessive electrode coupling: $F_t$>400 kHz The protocol 620 of FIG. 12*c* may be implemented in any appropriate manner. For instance, the impedance may be monitored to obtain the target phase frequency by sweeping the signal frequency (e.g., in accordance with the system 500 of FIG. 12*a*). This frequency sweep could be provided between two appropriate values (e.g., 50 kHz and 1 MHz) and using any appropriate incremental change between these values for the sweep (e.g., 10-20 kHz increments). This approach uses what may be referred to as frequency switching, which involves measuring the impedance one frequency at a time and rotating the frequencies by a frequency synthesizer or the like. Another approach would be to combine multiple frequencies together, and to determine the impedance at each of the individual frequencies from the combined signal through filtering. It should be appreciated that it may be such that interpolation will be required to determine the frequency associated with the target frequency condition in some cases (e.g., where the frequency associated with the target frequency condition is determined to exist between two frequencies used by the protocol 620).

The discussion above describes various implementations for determining a level of electrode coupling to a patient based on certain impedance related measurements such as phase angle. It will be appreciated that, while this is believed to be a particularly effective mechanism for obtaining electrode coupling information, other mechanisms may be utilized. Some of these mechanisms include other impedance-based measurement, mechanical vibration measurements (such as obtained from piezoelectric devices) or mechanical deformation measurements (such as obtained via a strain gauge). Thus, an indication of electrode positioning may be based on electrical, mechanical or other properties.

In any event, once an indication of electrode position has been obtained, it is desirable to convey this information to the physician. Moreover, as discussed above, it is useful to provide this information to the physician in a manner that minimizes distraction.

One aspect of the present invention relates to providing electrode coupling information or other information to a physician via electrode guidance instrumentation. In the following discussion, this is set forth in the context of providing outputs via the catheter handle set and/or a navigation system that can indicate any of multiple levels of electrode coupling such as insufficient coupling, sufficient coupling or elevated coupling. However, it will be appreciated that the invention is not limited to these specific contexts or implementations.

Figure 13:
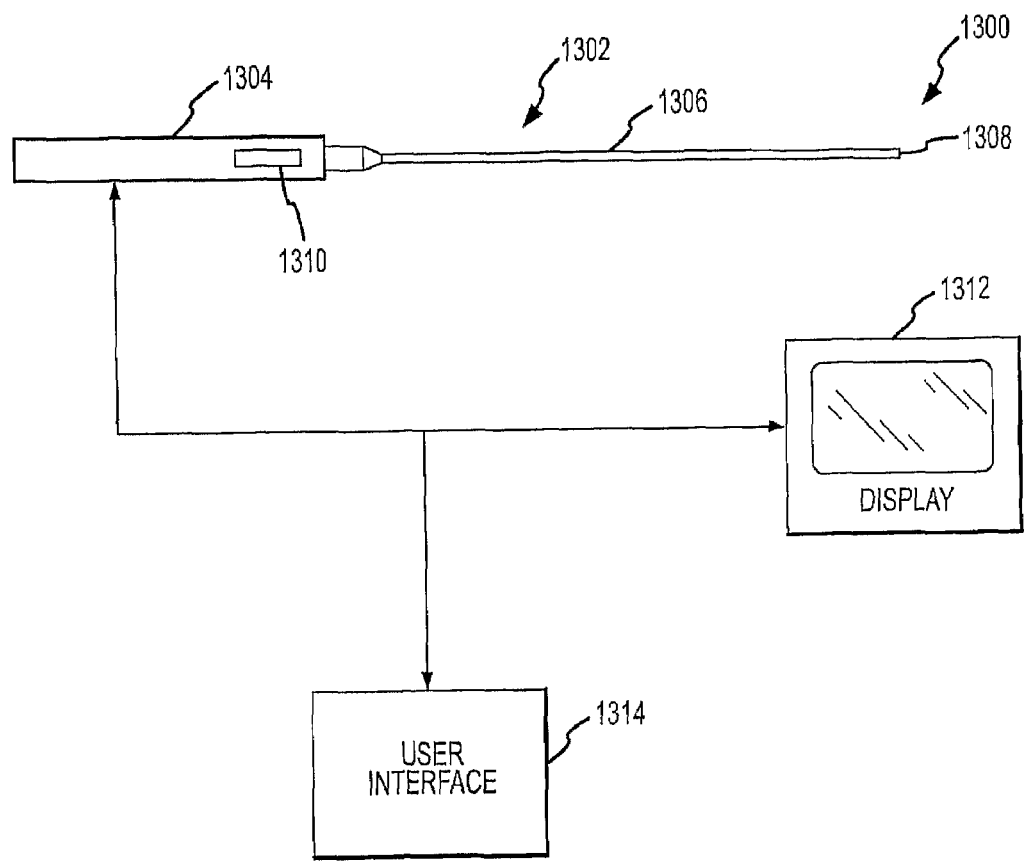
FIG. 13 is a schematic diagram of an electrode catheter system in accordance with the present invention.

Referring to FIG. 13, a catheter system 1300 in accordance with the present invention is shown. The system 1300 generally includes an electrode catheter 1302 that is operatively associated with a navigation system display 1312 and a user interface 1314. The illustrated electrode catheter 1302 includes an electrode 1308 for interacting with fluids and tissue of a patient, a handle set 1304 that can be gripped by a physician to advance withdraw, rotate or otherwise position the electrode 1308, and a catheter body 1306 extending between the handle set 1304 and the electrode 1308. The illustrated electrode catheter 1302 further includes an output device 1310 such as an LED array for providing an output concerning a level of electrode coupling, as will be discussed in more detail below.

The navigation system display 1312 provides visual information for assisting the physician in positioning the electrode 1308 in a desired position in relation to the patient. The navigation system will be described in more detail below. However, generally, the navigation system displays certain physiological structure of the patient, such as cardiac structure, based on electrical mapping, fluoroscopic and/or other information. Moreover, the position of the electrode 1308 is generally depicted on the display 1312 in relation to the physiological structure in order to assist the physician in directing the electrode 1308 to a desired position. It will thus be appreciated that the physician's visual attention is largely directed to the display during a medical procedure involving the electrode catheter 1302. However, skilled physicians will also deduce certain information regarding the electrode position based on tactile feedback through the handle set 1304.

The illustrated system also includes a user interface 1314 that the physician can utilize to input certain information regarding a procedure. For example, the physician may input information identifying the patient, the equipment utilized, the procedure being performed and the like. In addition, the physician may use the user interface 1314 to identify locations of interest, e.g., for ablation or the like. Thus, the user interface may include a keyboard, a graphical user interface or other input mechanisms.

Figure 14:
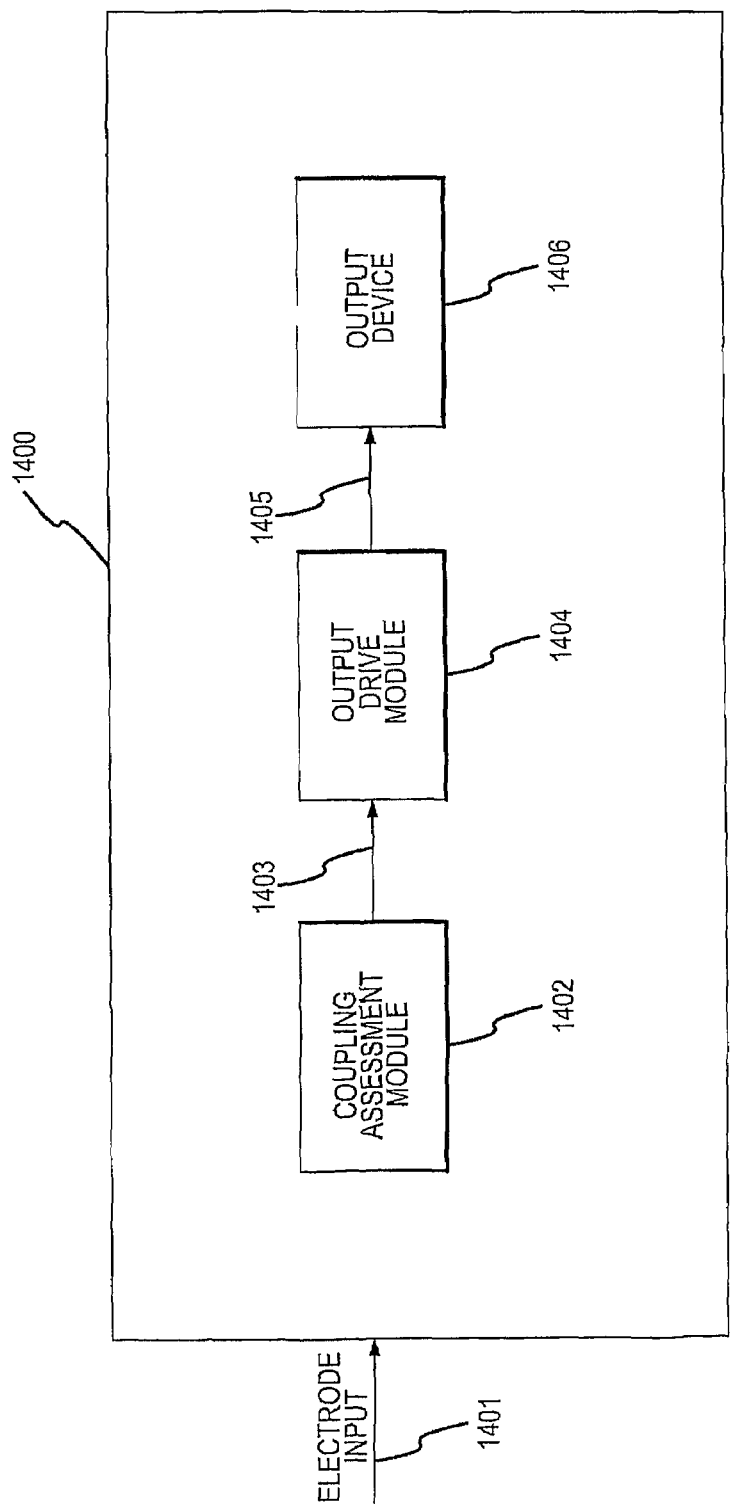
FIG. 14 is a schematic diagram of an electrode coupling output system in accordance with the present invention.

FIG. 14 is a schematic diagram of an electrode coupling output system 1400 in accordance with the present invention. The system 1400 receives an input 1401 indicative of a level of electrode coupling. For example, in implementations as discussed above, this input may provide information regarding phase angle. The system 1400 includes a coupling assessment module 1402, an output drive module 1404 and an output device 1406.

The coupling assessment module 1402 receives the input 1401 and determines a level of electrode coupling based on the input 1401. Depending on the implementation, the coupling assessment module 1402 may be capable of distinguishing between two or more levels of electrode coupling. The module 1402 may be embodied in a processor for executing logic to implement electrode coupling calculation as described above. The processor has appropriate I/O structure including an input interface for receiving the noted input 1401 and an output interface for transmitting control signals to the output drive module 1404. Thus, in certain implementations, the module 1402 may distinguish between insufficient coupling (e.g., corresponding to electrode contact with blood) and sufficient coupling (e.g., associated with tissue contact or electrical coupling sufficient for the desired procedure, such as ablation or mapping, regardless of physical contact). Alternatively, the module may distinguish between insufficient contact, sufficient contact and elevated contact (e.g., associated with potential penetration of the electrode through a chamber wall, which may or may not be desired). It will be appreciated that more levels may be defined, for example, representing additional contact levels or finer resolution between the noted contact levels.

Based on the determined coupling level, the coupling assessment module 1402 provides an output signal 1403 to the output drive module 1404. The output drive module generates a drive signal 1405 to drive an output device 1406 that provides an output to the physician, indicating the determined level of electrode coupling. As will be discussed in more detail below, various types of output devices may be utilized to provide this output to the physician. For example, an audio, visual or mechanical (e.g., vibration) indication may be provided via the handle set of the electrode catheter. Alternatively, an audio, visual or other indication may be provided to the physician via the navigation system. Accordingly, the nature of the output device 1406 varies depending on the specific implementation. Relatedly, the nature of the drive signal 1405 provided by the output drive module 1404 varies depending on the application, as will be described in more detail below.

Figure 15:
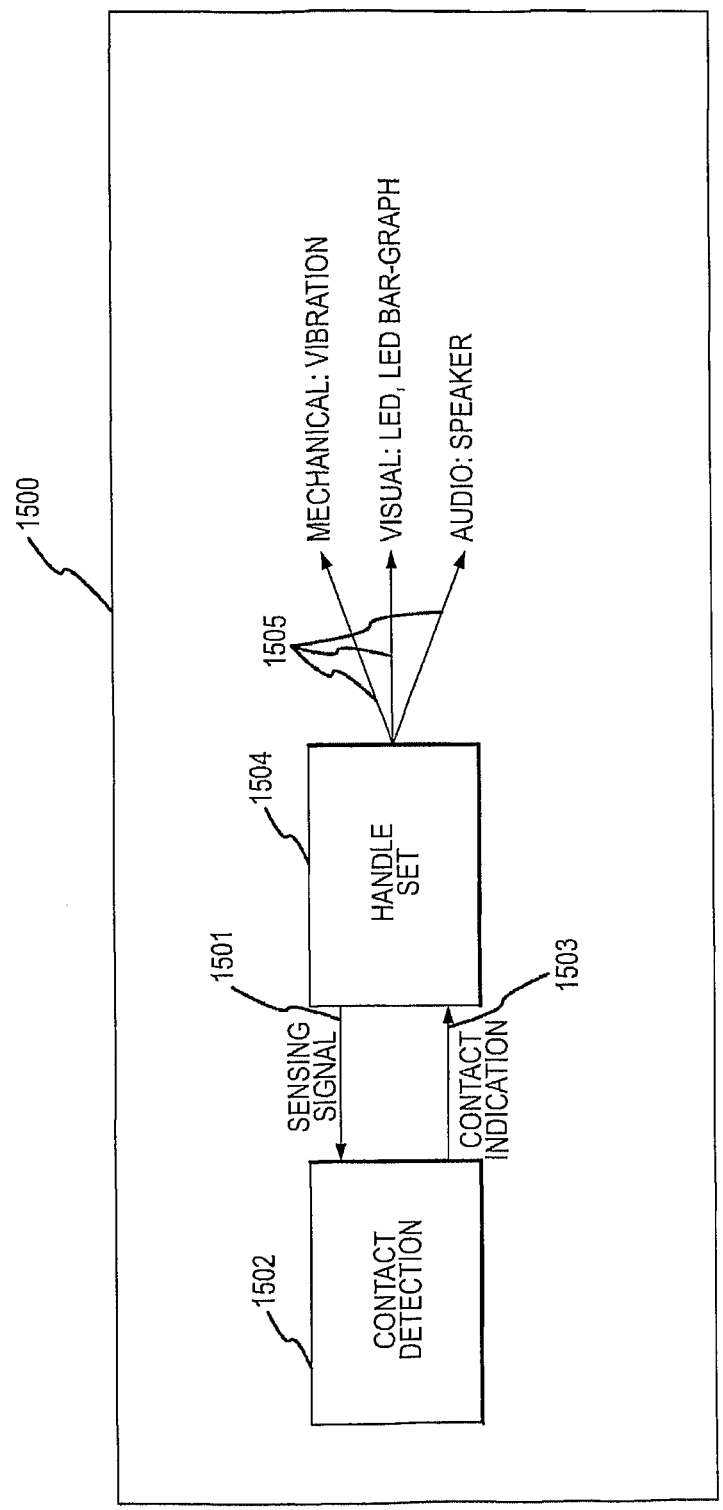
FIG. 15 illustrates a handle set based electrode coupling output system in accordance with the present invention.

As discussed above, an output indicating the determined level of electrode coupling may be provided to the physician via, for example, the handle set or the navigation system. FIG. 15 is a schematic diagram of a catheter system 1500 for providing such an output via the catheter handle set 1504. The illustrated system 1500 includes the handle set 1504 and a coupling detection module 1502. Although the coupling detection module 1502 is schematically illustrated as being separate from the handle set 1504, it will be appreciated that the module 1502 may be physically incorporated into the handle set 1504. In the illustrated system 1500, the handle set 1504, which is associated with the electrode of the electrode catheter, provides a sensing signal 1501 to the coupling detection module 1502. For example, in the case of a phase angle implementation, the sensing signal 1501 may include information sufficient to indicate phase angle relative to movement of the electrode. In that case, the detection module 1502 executes logic as described above to determine an electrode coupling level based on the phase angle information.

Based on this determination, a contact indication signal 1503 is provided to the handle set 1504. The handle set 1504 is then operative to provide an output 1505 to the physician, indicating the coupling level. Any suitable type of output may be used in this regard. For example, a mechanical output, such as a vibration of the handle set 1504, a visual output, such as an LED or LED bar graph, or an audio output, such as a variable tone (e.g., variable in pitch, volume or other audio parameter) may be utilized in this regard. Moreover, combinations of these types of outputs may be utilized. For example, a visual or audio output may be utilized to indicate an insufficient or sufficient level of electrode coupling, whereas a mechanical output may be used to indicate elevated electrode coupling. The type of output may be selected to minimize distraction to the physician or enhance physician awareness of the output. Again, it will be appreciated that the physician's visual attention may be primarily directed to a display of a navigation system during the medical procedure.

Figure 16:
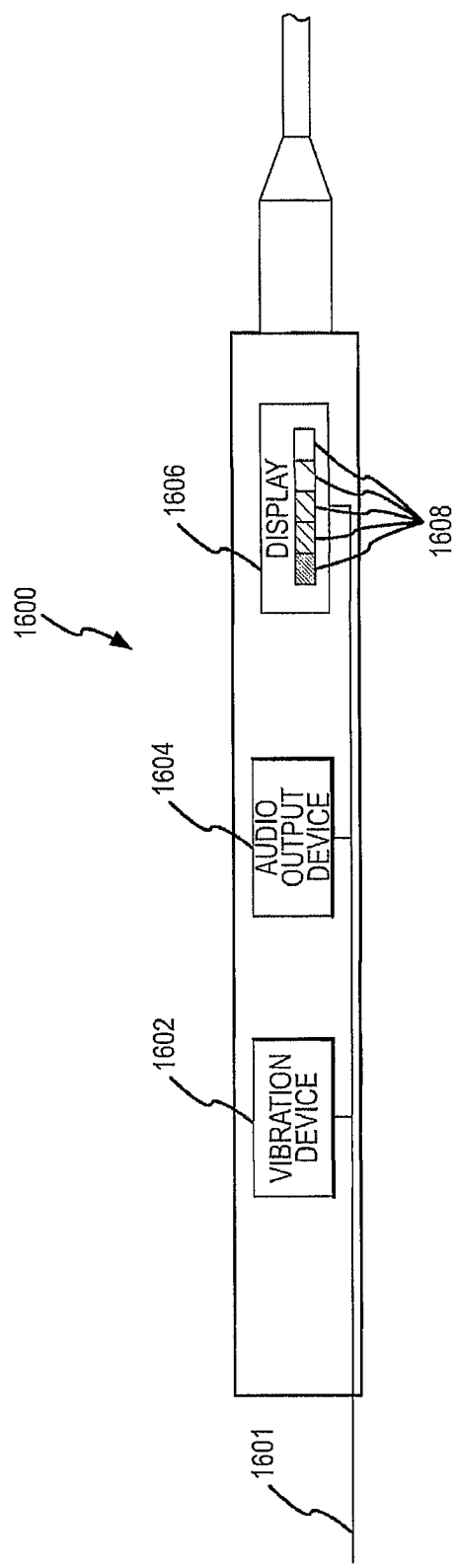
FIG. 16 illustrates a handle set incorporated various types of output devices in accordance with the present invention.

FIG. 16 is a partially schematic illustration of a handle set 1600 incorporating multiple output devices. The handle set receives an input signal 1601 from a coupling detection module. This signal 1601 is used to drive one or more of a vibration device 1602, an audio output device 1604, such as a tone generator, and a display 1606, in this case an LED bar graph. In this regard, the signal 1601 can be either a digital or analog signal. In the case of a digital signal, the signal may indicate yes/no information with regard to one or more coupling levels, e.g.: (1) insufficient contact (yes/no); (2) sufficient contact (yes/no); and (3) elevated contact (yes/no). Alternatively, the digital signal may indicate any of multiple coupling levels in step-wise fashion. That is, the digital signal may be encoded with information indicating the coupling level where such coding is based on a current level, voltage level, pulse sequence or other signal characteristic. In the case of an analog signal, the analog signal may be continuously variable to represent the electrode coupling level.

The vibration source 1602 is operative in response to the input signal 1601 to cause vibration of the handle set 1600 so as to provide electrode coupling information to the physician. For example, the device 1602 may be activated to indicate a particular coupling level, such as elevated contact. Alternatively, the vibration device may be operated at different frequencies or other parameters to indicate different electrode coupling levels.

The audio output device can output any suitable audio indication to identify the electrode coupling level. Thus, for example, where the input signal 1601 is an analog signal, the current, voltage or other parameter of the signal 1601 can be correlated to an electrode contact parameter such as phase angle. In response to the signal 1601, the pitch, volume or other parameter of a tone generated by the audio output device 1604 can be varied to directly correspond to the electrode coupling level.

The visual display 1606 can provide any suitable visual indication of the electrode coupling level. Thus, for example, the display 1606 may include a single LED, multiple LEDs or an LED bar graph. In the illustrated embodiment, the display comprises an LED bar graph, including multiple light segments 1608. Thus, for example, the voltage of the input signal 1601 can raise as a function of increasing electrode coupling. This raising voltage results in increased lighting of the light segments 1608 to provide a direct visual indication of electrode coupling level. Although FIG. 16 shows three separate output devices 1602, 1604 and 1606 in a single handle set 1600, it will be appreciated that a single type of output device may be utilized to indicate the electrode coupling level. Moreover, any combination of the illustrated output device types or other output device types may be utilized in this regard.

Figure 17:
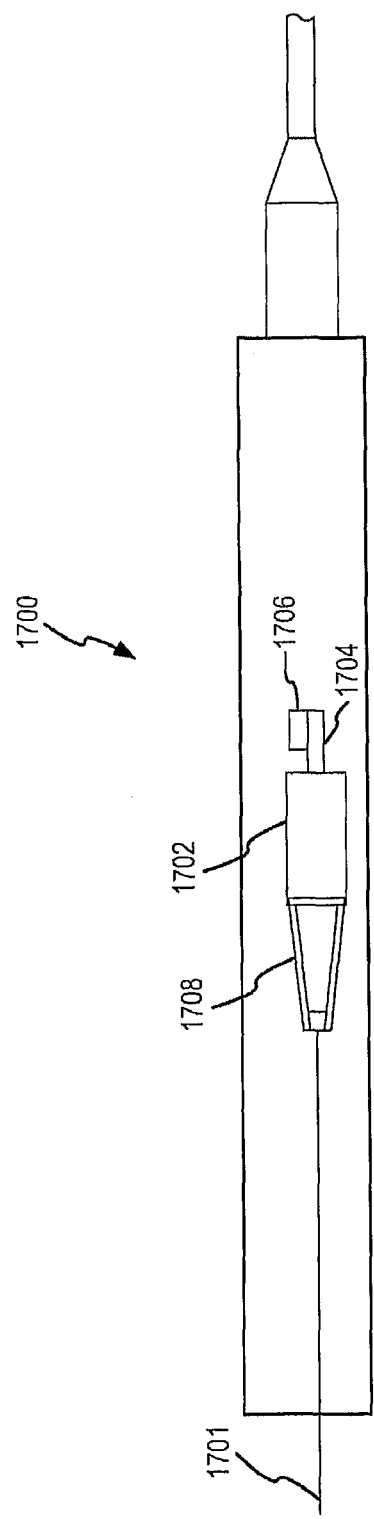
FIG. 17 illustrates a handle set incorporating a vibration device in accordance with the present invention.

FIG. 17 illustrates one embodiment of a mechanical vibration output device that may be utilized to indicate the electrode coupling level. It will be appreciated that vibration devices are well known and are used, for example, in connection with cell phones, pagers, control pads of video games and other existing products. A handle set 1700 incorporating such a vibration device is illustrated in FIG. 17. The vibration device of the handle set 1700 includes a motor 1702 that rotates an output shaft 1704. An unbalanced load 1706 is mounted on the output shaft 1704. Accordingly, operation of the motor 1702 to rotate the output shaft 1704 results in reciprocating forces associated with rotational movement of the unbalanced load 1706. The motor 1702 is mounted on a support structure 1708 that allows the motor 1702 to reciprocate in response to these forces. This, in turn, causes the handle set 1700 to vibrate. Accordingly, the motor 1702 receives an input signal 1701 indicating a level of electrode coupling. The motor 1702 can be activated or its operating parameters can be varied based on the input signal 1701 to provide an indication of the electrode coupling level. For example, the motor may be operative to vibrate the handle set 1700 only when a particular level of electrode coupling is indicated, such as elevated coupling. Alternatively, the operating speed of the motor 1702 or another parameter may be varied to indicate multiple levels of electrode coupling.

As noted above, during a medical procedure performed using the electrode catheter, the physician's visual attention is primarily directed to the navigation system. Accordingly, it has been recognized that an indication regarding the electrode coupling level may be provided (e.g., visually) via the navigation system in lieu of, or in addition to, the handle set indications described above. Certain implementations of such a system are described below.

Figure 18:
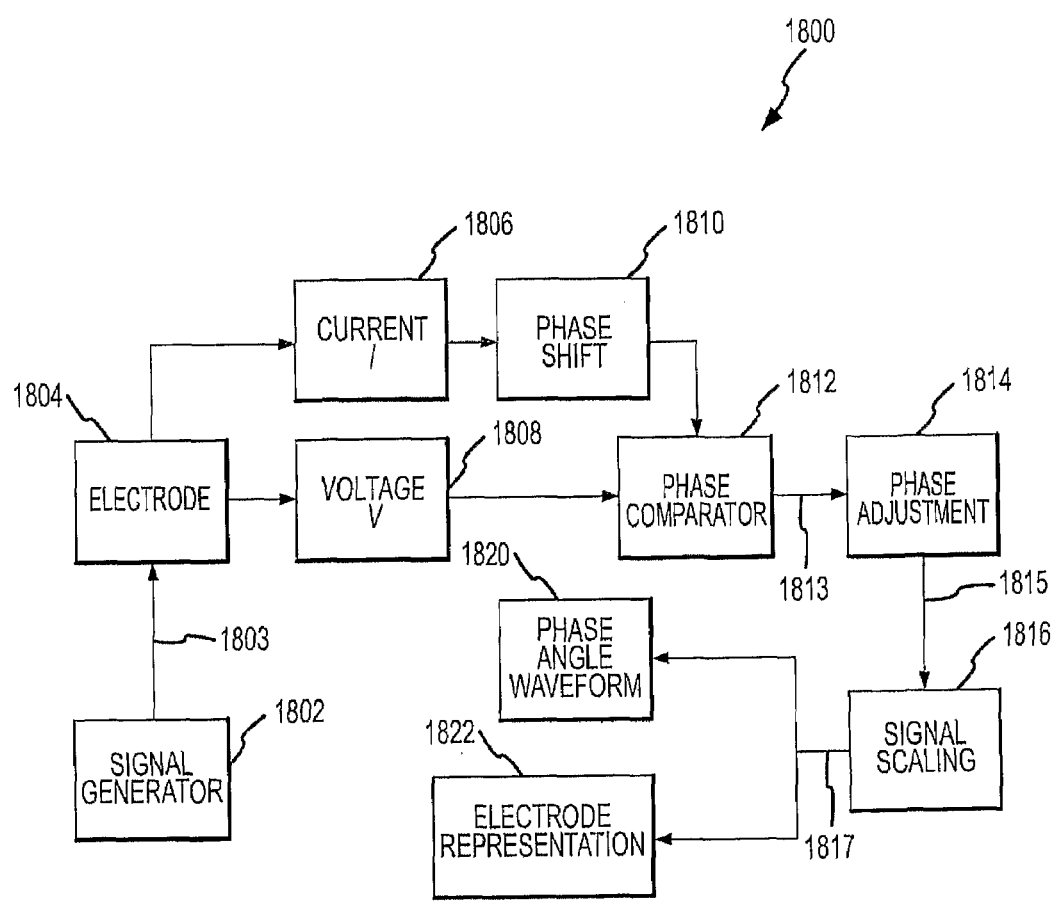
FIG. 18 is a schematic diagram of a navigation system based electrode coupling output system in accordance with the present invention.

FIG. 18 is a block diagram illustrating an electrode coupling assessment system 1800 that provides an indication of the electrode coupling level via a navigation system display. Although the level of electrode coupling may be determined in any appropriate manner, the illustrated system utilizes a phase angle measurement, as described above. The system 1800 includes a signal generator 1802 for generating a signal 1803 useful for making the phase angle measurement. As described above, the signal generator may be a dedicated signal generator for providing the electrode coupling assessment signal and/or a signal generator for providing a mapping, ablation or other procedure signal. The signal 1803 is applied to the patient via an electrode 1804 such as an ablation or mapping electrode.

The resulting current signal 1806 and voltage signal 1808 are compared by a phase comparator 1812. The phase comparator 1812 therefore provides an output signal 1813 indicative of a time series of phase angle values. Optionally, current measurements may be shifted by a phase shift circuit to facilitate operation of the phase comparator 1812 by "correcting" phase lag between the measured current and the measured voltage. Also optionally, output from the phase comparator 1812 may be "corrected" by a phase adjustment circuit to compensator for external factors, such as the type of grounding patch being used. The result is a phase angle signal 1815 indicative of the level of electrode coupling.

This signal 1815 can be displayed as a waveform and/or interpreted as an electrode contact level by an electro-anatomic mapping and navigation (EAMN) system or other procedure monitoring system (generically, "navigation system"). Examples of commercially available EAMN systems include the NAVX system of St. Jude Medical and the CARTO system of Johnson and Johnson. Fluoroscopic or other systems may also be used for procedure monitoring in this regard. The signal 1815 may therefore be scaled or otherwise processed by a signal scaling module 1816 to provide an input that can be properly handled by the navigation system. For example, the resulting signal 1817 may be voltage signal scaled to a range of 0-1V, a current signal scaled to 4-20 mA, or any other signal as required by the navigation system. In the illustrated implementation, this signal 1817 is used to provide a phase angle versus time waveform 1820 and is interpreted as a graphical electrode representation 1822 reflecting a level of electrode coupling.

Figure 19A:
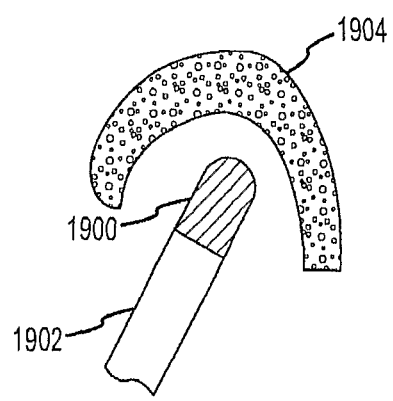
FIGS. 19A-20D illustrate graphical representations of an electrode in a navigation system display in accordance with the present invention.
Figure 19B:
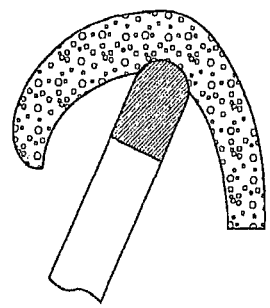
Figure 20A:
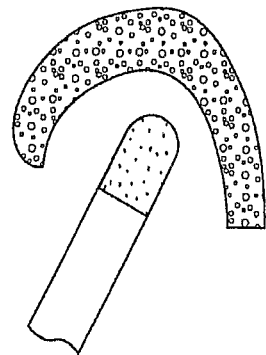
Figure 20B:
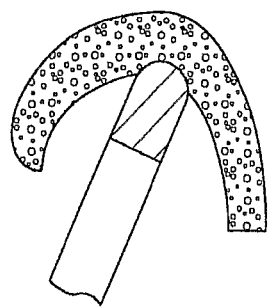
Figure 20C:
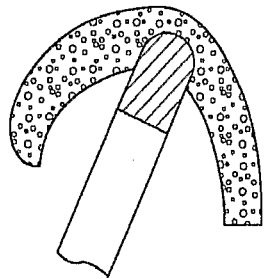
Figure 20D:
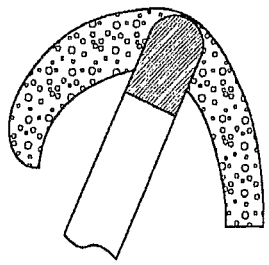

In the latter regard, the graphical electrode representation may reflect any of two or more levels of electrode coupling depending on the specific implementation. FIGS. 19A and 19B depict an exemplary implementation for indicating two possible electrode coupling levels, for example, indicating no physical tissue contact (e.g., the electrode is disposed in the patient's blood within a cardiac chamber) or tissue contact (e.g., the electrode is directly contacting cardiac tissue). Such two-state systems have been proposed by various parties.

FIGS. 19A and 19B show how these two electrode coupling conditions may be depicted on a display of a navigation system in accordance with the present invention. Specifically, FIG. 19A shows a condition where there is no physical contact between the electrode 1900 of catheter 1902 and the cardiac tissue 1904 of interest. This condition is detected by an electrode coupling detection system (a phase angle based system as described above or other system), and the associated electrode coupling level is communicated to the navigation system. The navigation system then uses this electrode coupling level to select a display parameter (e.g., a color) for the electrode 1900. For example, the electrode may be depicted in blue (represented as lighter shading in FIG. 19A) for the no contact condition and in red (represented as darker shading in FIG. 19B) for the direct physical contact condition.

Other systems may be capable of detecting and indicating more than two levels of electrode coupling, as shown in FIGS. 20A-20D. In this case, four levels of coupling, which may be designated no coupling (FIG. 20A), light coupling (FIG. 20B), hard coupling (FIG. 20C) and elevated coupling (FIG. 20D) are detected and shown in the display as different electrode colors (represented by different shading in FIGS. 20A-20D). Any colors can be used to designate the levels no coupling, light coupling, hard coupling and elevated coupling, such as white, green, yellow and red, respectively. In the case of a phase angle implementation, theses levels may be defined by corresponding phase angle ranges. Although the increasing electrode coupling levels of FIGS. 20A-20D are shown as corresponding to increasing levels of physical contact, it is noted that electrode coupling, including significant levels of coupling, can be achieved without physical contact.

Figure 21:
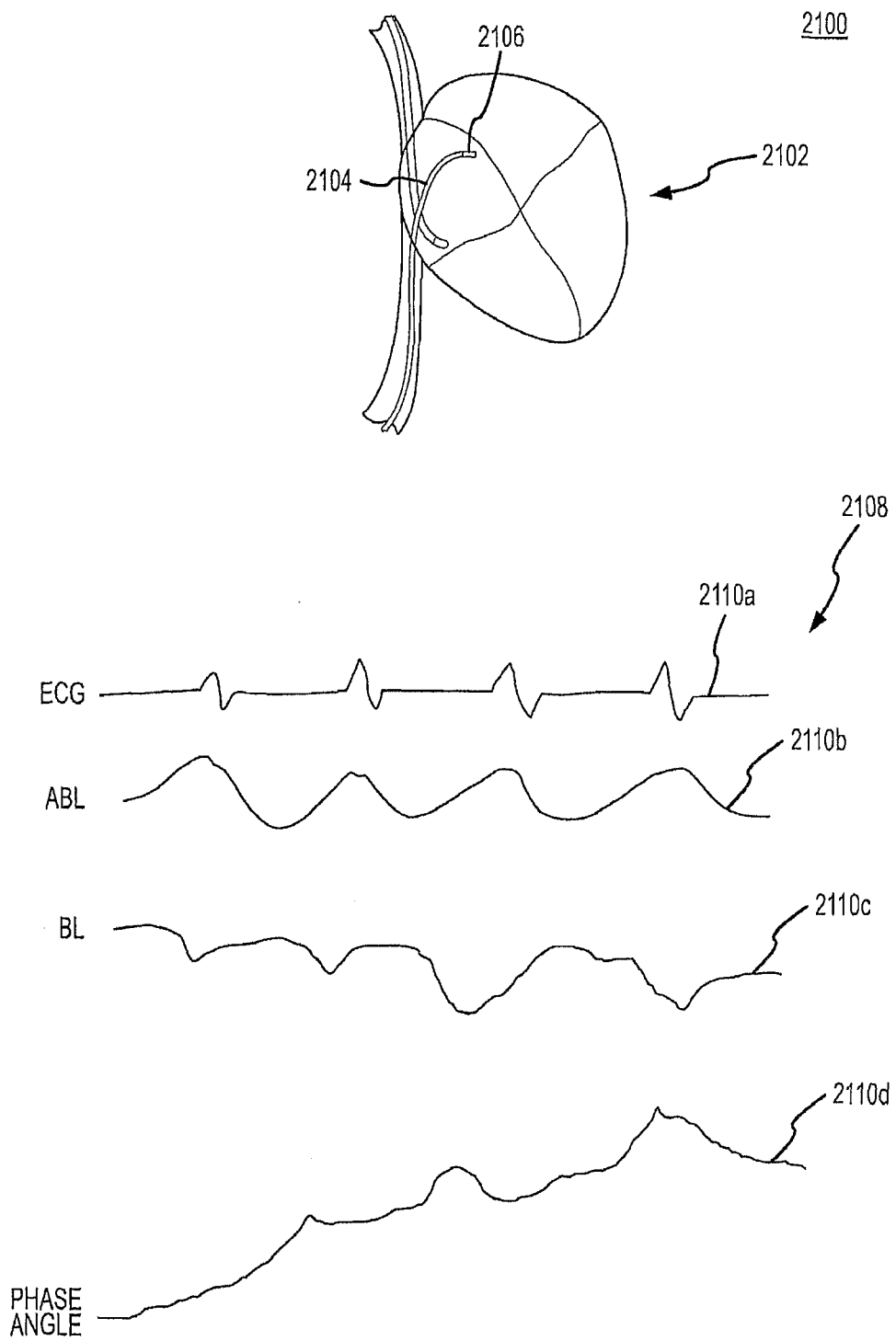
FIG. 21 illustrates a navigation system display in accordance with the present invention.

Other types of display representations may be used to provide the electrode coupling level information in connection with a navigation system display. For example, physicians in this field tend to be comfortable with and to derive a substantial amount of information from waveform data. Indeed, it is common to provide an ECG waveform or other waveforms on the navigation system display. FIG. 21 illustrates a display screen 2100, including imaging portion 2102 depicting a catheter 2104 with an electrode 2106 (which may change colors to indicate the electrode coupling level) and a waveform portion 2108 showing various waveforms 2110a-2110d. For example, these waveforms may include an ECG waveform 2110a, a waveform showing the signal detected by an ablation electrode 2110b (which can be the same as electrode 2106), a waveform detected by a reference electrode 2110c (e.g., another electrode on the catheter 2104, an electrode on another catheter or an external return electrode patch) and a phase angle waveform 2110d.

In this case, the phase angle waveform 2110*d* shows not only the magnitude of the phase angle at a given time, but also the trend or change in magnitude over time which may assist a physician in evaluating the electrode coupling level or provide other useful information (e.g., to evaluate the quality of a lesion formed by ablation). The waveform may be a raw waveform reflecting each successive determined value of phase angle. Alternatively, the waveform 2110*d* may be filtered to remove noise such as artifact associated with patient motion or provide averaging. Thus, in the illustrated example, the waveform includes plethysmographic features reflecting variations in electrode coupling due to movement of the beating heart. This may be useful to a physician in evaluating the electrode coupling (e.g., the level or modulation in this regard, as visually discerned by the physician or calculated, for example, by spectral analysis, may be indicative of the level of electrode coupling) or otherwise. Alternatively, such waveform features may be eliminated by applying an appropriate low pass filter to remove these components and provide a degree of averaging. Such filtering or averaging may also be desired in relation to outputting electrode coupling level information (e.g., via displayed electrode color) so as to avoid elevated output flicker.

Figure 22:
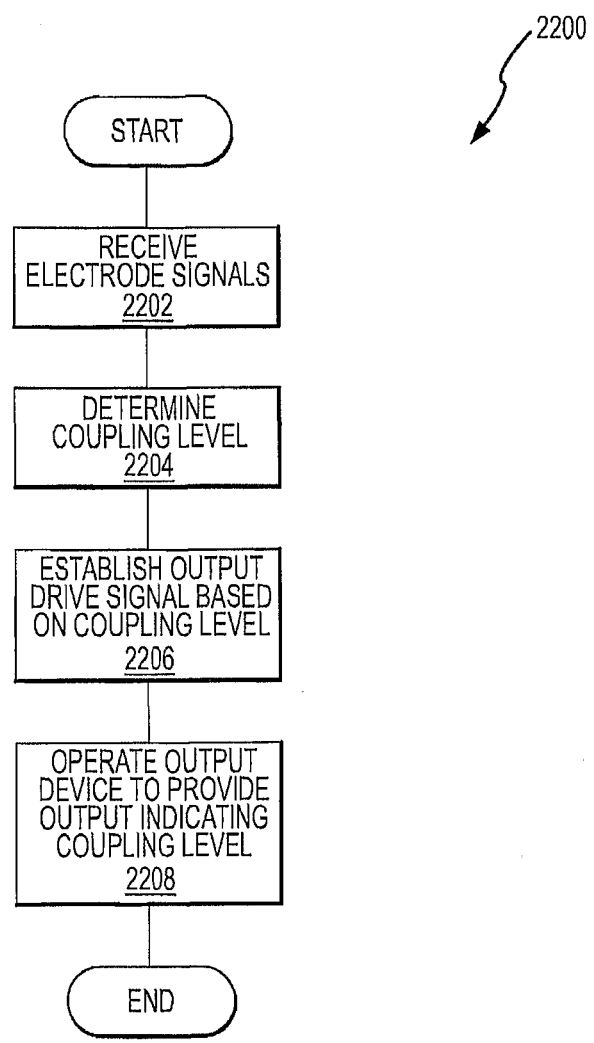
FIG. 22 is a flow chart illustrating a process for outputting electrode coupling information via guidance instrumentation in accordance with the present invention.

A number of implementations for providing an indication of electrode contact level via electrode guidance instrumentation (e.g., the handle set and/or the navigation system) have thus been described. The associated functionality can be summarized by reference to the flow chart of FIG. 22. The illustrated process 2200 is initiated by receiving (2202) current and voltage signals associated with the electrode under consideration and determining a phase angle value. This value can then be used to determine (2204) an electrode coupling level. Information regarding this coupling level can be provided to the physician in various ways via the handset (an audio, visual and/or mechanical output) and/or via a navigation system display. Accordingly, an appropriate drive signal is established (2206) depending on the nature of the output device. In any event, the output indicates an electrode cooling level of two or more possible coupling levels. The output device is thereby operated (2208) to provide an output indicating the determined electrode coupling level.

Although a number embodiments of this invention have been described above with a certain degree of particularity, those skilled in the art could make numerous alterations to the disclosed embodiments without departing from the spirit or scope of this invention. For example, the levels of electrode coupling may be determined via various technologies. Moreover, certain aspects of the invention are applicable in other contexts. For example, an output device may be incorporated into an electrode catheter to provide any information of interest and is not limited to providing electrode coupling information. All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed:

1. A method for use in operating an electrode catheter, the method comprising the steps of:
   establishing an electrode coupling assessment system for evaluating an ablation energy level passing between an ablation electrode and patient tissue, said assessment system being operative to, based on impedance-related values and predetermined tissue specific benchmark values, distinguish between at least two different ablation energy ranges, wherein said ablation energy ranges include an insufficient ablation energy range for lesion formation and an elevated ablation energy range for lesion formation, where said elevated ablation energy range indicates potential for tissue damage;
   operating said electrode coupling assessment system in connection with application of ablation energy to said ablation electrode to identify a current ablation energy level of passing between said ablation electrode and patient tissue; and
   providing a first mechanical output, via a handle set of said electrode catheter used by a physician in guiding said electrode in relation to physiological structure of said patient, upon identifying said current ablation energy level as being in said elevated ablation energy range.

2. The method as set forth in claim 1, wherein said electrode coupling assessment system is operative to distinguish between each of said insufficient ablation energy range for lesion formation, a sufficient ablation energy range for lesion formation and said elevated ablation energy range for lesion formation.

3. The method as set forth in claim 1, wherein said electrode coupling assessment system is operative for distinguishing between said ablation energy ranges based on a relationship between values related to resistance and reactance components of impedance.

4. The method as set forth in claim 1, further comprising: providing a visual output, via said handle set of said electrode catheter, indicating said current ablation energy level.

5. The method as set forth in claim 1, wherein said first mechanical output comprises a vibratory output.

6. The method as set forth in claim 1, further comprising:
   providing a second mechanical output, via said handle set of said electrode catheter, upon identifying said current ablation energy level as being in said insufficient ablation energy range, where said first mechanical output and said second mechanical output are different.

7. An apparatus for use in operating an electrode catheter, the apparatus comprising:
   an input interface operative to receive an impedance-related signal during an ablation procedure that is indicative of a level of ablation energy passing between an electrode of said electrode catheter and patient tissue;
   a processor operative to process said impedance-related signal in relation to empirically predetermined tissue specific benchmark values for a specific procedure to determine a current level of ablation energy and categorize said current level of ablation energy as being in ranges of insufficient ablation energy for lesion formation, sufficient ablation energy for lesion formation, and elevated ablation energy for lesion formation, where said elevated ablation energy for lesion formation indicates potential for tissue damage; and
   an output module operative to generate a first output signal for receipt by a vibratory output device incorporated into a handle set of said electrode catheter, where said first output signal is operative to cause said vibratory output device to generate vibrations upon said current level of ablation energy being categorized in said range of said elevated ablation energy.

8. The apparatus as set forth in claim 7, wherein said processor is operative for distinguishing between said ranges of insufficient ablation energy for lesion formation, sufficient ablation energy for lesion formation, and elevated ablation energy for lesion formation based on the relationship between values related to resistance and reactance components of impedance.

9. The apparatus as set forth in claim 7, wherein the output module is further operative to generate a visual output signal so as to indicate, via an visual output interface incorporated into a handle set of said electrode catheter, said current ablation energy level.

10. The apparatus as set forth in claim 7, wherein said output module is operative to generate multiple different output signals corresponding to multiple different ablation energy ranges, wherein said multiple different output signals are operative to cause said vibratory output device to generate different vibratory outputs corresponding to said current level of ablation energy.

11. An electrode catheter system comprising:
an electrode;
a catheter associated with said electrode;
a power source operative to provide ablation energy to said electrode;
guidance instrumentation for guiding said electrode relative to tissue of a patient, said guidance instrumentation including a navigation system operative to monitor a position of said electrode and a manipulation system operative to control a position of said electrode, wherein said manipulation system includes a handle set of said electrode catheter, said handle set including mechanical output device; and
a processor operative to receive impedance related signal information from said electrode during application of said ablation power and, based on empirically predetermined tissue specific benchmark values for a specific procedure, said processor being further operative to determine an ablation energy level between said electrode and a patient and categorize said ablation energy level in one of at least two different tissue specific ablation energy ranges including a range of insufficient ablation energy for lesion formation and a range of elevated ablation energy for lesion formation, where said range of elevated ablation energy indicates potential for tissue damage, said processor further being operative to control said output device of said handle set and said navigation system to provide a first mechanical indication upon identification of said ablation energy level being in said range of insufficient ablation energy and a second mechanical indication upon identification of said ablation energy level being in said range of elevated ablation energy, where said first and second mechanical indications are different.

12. The electrode catheter system as set forth in claim 11, wherein said processor is operative for distinguishing between each of said range of insufficient ablation energy for lesion formation, a range of sufficient ablation energy for lesion formation, and said range of elevated ablation energy for lesion formation.

13. The electrode catheter system as set forth in claim 11, wherein said processor is operative for distinguishing between said ranges based on a relation between values related to resistance and reactance components of impedance.

14. The electrode catheter system as set forth in claim 11, further comprising:
said processor further being operative to control said output device of said handle set and said navigation system to provide a visual indication of said ablation energy level.

\* \* \* \* \*